United States Patent
Bosch et al.

(10) Patent No.: US 10,022,303 B2
(45) Date of Patent: Jul. 17, 2018

(54) INHALABLE PHARMACEUTICAL COMPOSITIONS

(71) Applicants: H. William Bosch, Bryn Mawr, PA (US); Matthew Callahan, King of Prussia, PA (US); Felix Meiser, Claremont (AU); Marck Norret, Darlington (AU); Adrian Russell, Rivervale (AU)

(72) Inventors: H. William Bosch, Bryn Mawr, PA (US); Matthew Callahan, King of Prussia, PA (US); Felix Meiser, Claremont (AU); Marck Norret, Darlington (AU); Adrian Russell, Rivervale (AU)

(73) Assignee: iCeutica Pty Ltd., Iluka, WA (AU)

( * ) Notice: Subject to any disclaimer, the term of this patent is extended or adjusted under 35 U.S.C. 154(b) by 0 days.

(21) Appl. No.: 13/781,115

(22) Filed: Feb. 28, 2013

(65) Prior Publication Data
US 2014/0065219 A1    Mar. 6, 2014

Related U.S. Application Data

(60) Provisional application No. 61/604,435, filed on Feb. 28, 2012.

(51) Int. Cl.
*A61K 9/00* (2006.01)
*A61K 31/00* (2006.01)
*A61J 3/02* (2006.01)
*A61K 31/137* (2006.01)
*A61K 31/46* (2006.01)

(52) U.S. Cl.
CPC .............. *A61J 3/02* (2013.01); *A61K 9/0075* (2013.01); *A61K 31/137* (2013.01); *A61K 31/46* (2013.01)

(58) Field of Classification Search
CPC .. A61K 9/0075; A61K 9/145; A61K 2300/00; A61K 9/0073; A61K 31/137; A61K 31/46; A01N 25/12; A61J 3/02
See application file for complete search history.

(56) References Cited

U.S. PATENT DOCUMENTS

| | | | |
|---|---|---|---|
| 4,169,603 A * | 10/1979 | Funk | 277/348 |
| 5,478,705 A | 12/1995 | Czekai et al. | |
| 5,500,331 A | 3/1996 | Czekai et al. | |
| 5,718,388 A * | 2/1998 | Czekai et al. | 241/21 |
| 6,634,576 B2 * | 10/2003 | Verhoff et al. | 241/21 |
| 8,182,838 B2 * | 5/2012 | Morton et al. | 424/489 |
| 2004/0047810 A1 * | 3/2004 | Staniforth et al. | 424/46 |
| 2005/0220887 A1 * | 10/2005 | Herbert et al. | 424/489 |
| 2006/0257491 A1 * | 11/2006 | Morton et al. | 424/489 |
| 2008/0248119 A1 * | 10/2008 | Kawashima et al. | 424/489 |
| 2010/0055049 A1 | 3/2010 | Kuo et al. | |
| 2011/0139152 A1 * | 6/2011 | Morton et al. | 128/203.15 |
| 2012/0138056 A1 * | 6/2012 | Morton et al. | 128/203.15 |

FOREIGN PATENT DOCUMENTS

| | | |
|---|---|---|
| AU | 2009100698 | 8/2009 |
| WO | WO 1998/015280 | 4/1998 |
| WO | WO 1999/053901 | 10/1999 |
| WO | WO 2001/89491 | 11/2001 |
| WO | WO 2005/025541 | 3/2005 |
| WO | WO 2005/089717 | 9/2005 |
| WO | WO 2009/056851 | 5/2009 |
| WO | WO 2010/111680 | 9/2010 |
| WO | WO2010/121323 | 10/2010 |
| WO | WO 2010121323 A1 * | 10/2010 |

OTHER PUBLICATIONS

Islam et al., "Adhesion and dispersion of salmeterol xinofoate from lactose interactive mixtures for inhalation—can surface roughness of carriers determine performance," Chemeca 2009:Engineering our Future: Are We up to the Challenge, 27-30, Sep. 2009.
Adi et al., "Micro-particle corrugation, adhesion and inhalation aerosol efficiency," European Journal of Pharmaceutical Sciences, Sep. 2008, 35:12-18.
Adi et al., "Scanning White-Light Interferometry as a Novel Technique to Quantify the Surface Roughness of Micron-Sized Particles for Inhalation," Langmuir, 2008, 24: 11307-11312.
Almarasson et al., "Crystal Engineering of the Composition of Pharmaceutical Phases. Do Pharmaceutical Co-crystals Represent a New Path to Improved Medicines?" The Royal Society of Chemistry, Sep. 2004, 17:1889-1896.
International Preliminary Report on Patentability in International Application No. PCT/IB2013/000708, dated Sep. 2, 2014, 5 pages.
International Search Report and Written Opinion in International Application No. PCT/IB2013/000708, dated Aug. 29, 2013, 9 pages.
Son et al., "Optimization of an In Vitro Dissolution Test Method for Inhalation Formulations," Dissolution Technologies, May 2010, 17(2): 6-13.
Examination Report for corresponding Application No. 13729407. 0, dated Jan. 20, 2016, pp. 1-4.

* cited by examiner

*Primary Examiner* — Robert A Wax
*Assistant Examiner* — Olga V Tcherkasskaya
(74) *Attorney, Agent, or Firm* — Fish & Richardson P.C.

(57) ABSTRACT

Methods for making inhalable composite particles comprising a pharmaceutically-active agent, the method comprising: a) providing composite particles comprising a millable grinding matrix and a solid pharmaceutically-active agent, wherein the pharmaceutically-active agent has an median particle size on a volume average basis between 50 nm and 3 μm; and b) milling the composite particles in a mill without milling bodies for a time period sufficient to produce inhalable composite particles having a mass median aerodynamic diameter between 1 μm and 20 μm are described.

8 Claims, 2 Drawing Sheets

INHALABLE PHARMACEUTICAL COMPOSITIONS

RELATED APPLICATION

Figure 1:
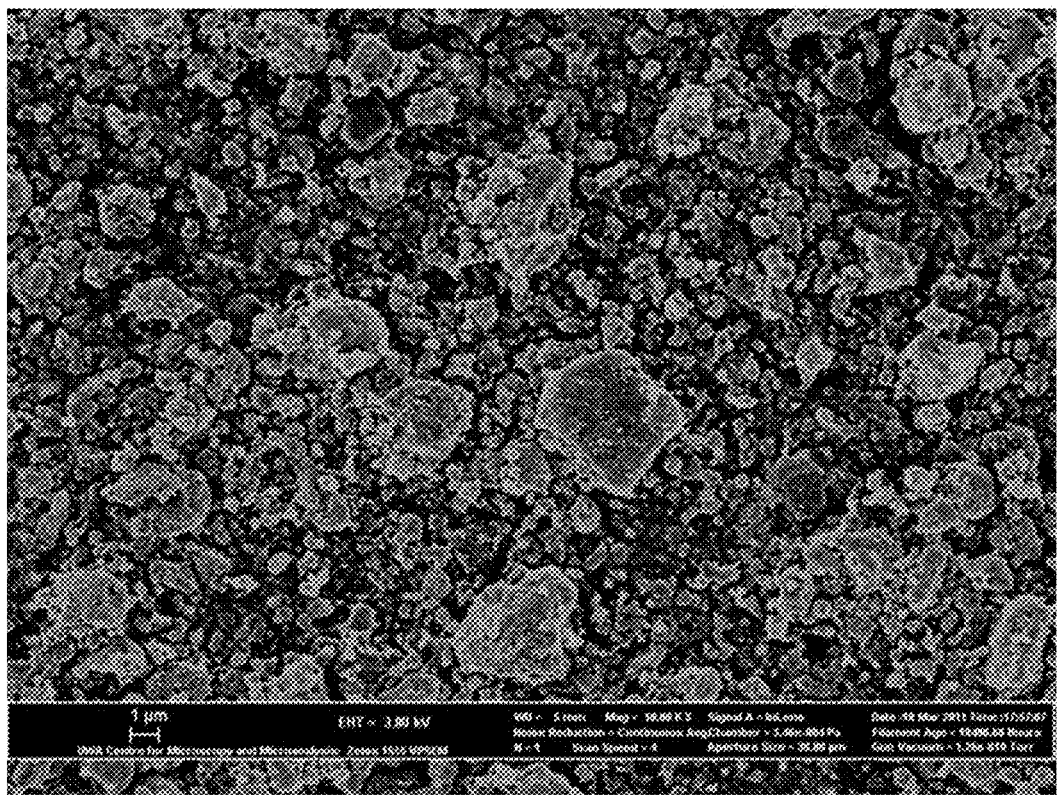

This application claims priority to U.S. Provisional Application No. 61/604,435, which was filed Feb. 28, 2012.

BACKGROUND

The rationale for delivering drugs via inhalation varies from class to class. For example, due to the nature of certain respiratory disease states such as infection, inflammation, or bronchoconstriction, it has been found that inhalation is the optimal route of administration to achieve sufficiently high levels of drug in the diseased tissue(s). In some cases, certain agents delivered via inhalation can produce fewer systemic side effects when inhaled, without comprising efficacy, as is the case for some classes of respiratory therapeutics. On the other hand, drugs intended for systemic activity may be delivered via inhalation to take advantage of the high surface area of the lungs, providing rapid drug absorption into the systemic circulation without first pass metabolic effects associated with oral administration. In some situations, delivery of an agent to the lung may be for the convenience of either the patient or healthcare provider. There is currently interest in the development of vaccine delivery to the lungs, which if successful would remove the need for injections as part of routine vaccination. Common medicaments delivered to the lung are drugs for the treatment of asthma and chronic obstructive pulmonary disease (COPD) where the drugs act locally in the lung tissue to prevent or relieve symptoms such as bronchial spasm. Another example would be the delivery of antibiotics to treat the presence of bacterial infections of the lung.

At present there are generally three different methods used for delivery of drugs to the lung. The first involves drug substance dissolved or dispersed in a liquid/gas propellant such as a chlorofluorocarbon (CFC) or hydrofluorocarbon (HFA134a). In these systems, the drug substance and propellant are supplied in a canister which contains a metering valve, the canister being used in conjunction with a device referred to as a pressurized metered dose inhaler (pMDI). At the time of administration, patients are required to coordinate their breath inhalation with actuation of the device. When the device is actuated, the drug substance is aerosolized by the propellant. Pressurized metered dose inhalers have certain disadvantanges which include (in some cases) the use of ozone-depleting propellants (CFCs). Also, upon actuation the drug substance particles exit the devices at high velocities due to the pressures generated by the propellants. This causes much of the dose to impact the patient's throat and be swallowed instead of being delivered to the airways of the lung. Many patients also have difficulty coordinating their breathing with actuation of the devices. For all of the above mentioned reasons, pressurized metered dose inhalers are less than optimal for delivery of drug substance to the lung.

A second method of pulmonary drug delivery involves dissolution or dispersion of the drug substance in water followed by nebulization of the solution or suspension with a compressed air (jet) or ultrasonic nebulizer. This approach is often preferred for pediatric patients who are unable to coordinate their breathing with actuation of a pressurized metered dose inhaler. Drug delivery by nebulization suffers from the disadvantage of being very slow. Typical commercially available nebulizers have delivery rates in the range of ca. 0.25 to 0.50 mL/min, leading to drug administration times of 6 to 7 minutes or longer. Nebulization therapy is inconvenient and requires a high level of patient compliance. For instance, all nebulizers have to be washed and disinfected after each use. Jet nebulizers require the use of an electrically operated air compressor, and ultrasonic nebulizers must be connected to line voltage or require batteries for operation. Some nebulizers which contain mesh screens are only suitable for delivery of drug solutions and cannot be used with suspensions. For all of these reasons, nebulizer use is generally limited to patients who cannot coordinate their breathing with device actuation and to hospitalized patients with breathing tubes in place.

The third method of pulmonary drug delivery is by the inhalation of a dry powder formulation. Drug substance is delivered to the lungs by the patient breathing in the powder from a delivery device positioned in the mouth. Typical dry powder formulations consist of carrier particles of an inert ingredient such as lactose blended with micronized pharmaceutically active agent, although some devices are designed to deliver pure micronized drug substance. The most important property for successful delivery of dry powder inhaled therapeutics is the aerodynamic size of the aerosolized drug particles. Aerodynamic size is a measure of how drug particles behave in an air stream and depends on a variety of factors including the geometric particle size, shape, and density. Aerodynamic size also depends on how readily the particles in a powder can be separated or deaggregated from each other when aerosolized. Thus, small particles which are strongly aggregated may behave like much larger particles when aerosolized. The aerodynamic size determines how far into the lung the particles may penetrate. In general the smaller the particle size, the deeper the particles penetrate into the lung. Inhaled particles smaller than about 1 µm in diameter often do not deposit in the lung but are exhaled back out of the lung. For drugs intended for systemic absorption, deep penetration into the alveolar region of the lung is necessary and particles having an MMAD of 0.5 to 5 (or 1 to 3) µm are generally desirable. For treating COPD, asthma and other diseases of the respiratory tract, topical delivery to upper airways is the aim. Particles with a size of 3 to 5 µm are generally preferred for this purpose because they tend to deposit in the conducting airways of the lung. Most raw drug substance is considerably larger than 1 to 5 µm in diameter, therefore the current methods of making formulations for inhalation requires air jet micronization of the drug substance. Micronization is an effective method of reducing drug particle size, but it tends to impart high levels of electrostatic charge on the particles which causes them to adhere to each other, to carrier particles in the formulation, and to surfaces of dry powder inhaler devices. As a result, the delivery efficiency of conventional dry powder formulations can be relatively low, and in some cases as little as one third of the aerosolized material may be able to reach the patient's respiratory tract.

There are several other critical parameters for successfully delivering therapeutic or pharmaceutical agents by dry powder inhalation. One important parameter is the aerodynamic diameter of the particles, which is a measure of how the particles behave when dispersed in an air stream. In cases where the formulation contains excipients in addition to active agent particles, adequate content uniformity of the powder is another important attribute for accurate delivery of dose. Another critical parameter for inhaled dry powder formulations is the flowability of the powder. The powder in the device used by the patient needs to flow well, so that a full and consistent dose of the powder formulation leaves the device. A further critical parameter for inhaled dry powder formulations is the efficiency of dose delivery, a measure of which is the fine particle fraction (FPF). Thus, the FPF provides an in vitro measure of the efficiency of the device/formulation in delivering the active to the lung.

Despite advances in methods of preparing dry powder formulations, there remains a need for particles with the appropriate properties, such as size, uniformity, flowability, and FPF, for enhanced delivery of therapeutics to the lung. Furthermore, methods are needed which can be readily utilized without limitations imposed by the solubility of the therapeutic agent and are cost-effective to manufacture. These needs and other needs are satisfied by the present invention.

SUMMARY

Described herein is a method for making inhalable composite particles comprising a pharmaceutically-active agent, the method comprising: a) providing composite particles comprising a millable grinding matrix and a solid pharmaceutically-active agent, wherein the pharmaceutically-active agent has an median particle size on a volume average basis between 50 nm and 3 µm; and b) milling the composite particles in a mill without milling bodies for a time period sufficient to produce inhalable composite particles having a mass median aerodynamic diameter between 1 µm and 20 µm.

In various aspects: inhalable composite particles comprise a solid pharmaceutically-active agent having a median particle on a volume average basis between 50 nm and 3 µm; the inhalable composite particles have a median particle size on a volume average size less than or equal to 10,000 nm; the inhalable composite particles have a D90, determined on a particle volume basis, less than or equal to 15,000 nm; the inhalable composite particles have a D90, determined on a particle volume basis, greater than or equal to 2000 nm; the inhalable composite particles have a volume weighted mean (D4,3) less than or equal to 10,000 nm; the inhalable composite particles have a volume weighted mean (D4,3) greater than or equal to 1000 nm; the inhalable composite particles are capable of providing an aerosol with a mass median aerodynamic diameter (MMAD) of the inhalable composite particles between 1 µm and 10 µm when delivered from a dry powder inhaler; the inhalable composite particles are capable of providing an aerosol with a fine particle fraction (FPF) of emitted dose of the pharmaceutically active agent of greater than or equal to about 10% when delivered from a dry powder inhaler; the inhalable composite particles are capable of providing an aerosol with a related standard deviation (RSD) of the FPF of emitted dose of the pharmaceutically active agent of less than or equal to about 10%; the inhalable composite particles are capable of providing an aerosol with a fine particle fraction (FPF) of total recovered dose of the pharmaceutically active agent of greater than or equal to about 30% when delivered from a dry powder inhaler; the inhalable composite particles when delivered from a dry powder inhaler are capable of providing an aerosol with a mass median aerodynamic diameter (MMAD) of the inhalable composite particles from about 1 µm to about 10 µm and a FPF of the pharmaceutically active agent of at least about 10%.

In various aspects: the inhalable composite particles are capable of providing an aerosol with a mass median aerodynamic diameter (MMAD) of the inhalable composite particles between 1 µm and 7 µm when delivered from a dry powder inhaler; the inhalable composite particles are capable of providing an aerosol with a mass median aerodynamic diameter (MMAD) of the inhalable composite particles between 1.5 µm and 5 µm when delivered from a dry powder inhaler; the inhalable composite particles are capable of providing an aerosol with a mass median aerodynamic diameter (MMAD) of the inhalable composite particles is between 2 µm and 5 µm when delivered from a dry powder inhaler; the inhalable composite particles are capable of providing an aerosol with a mass median aerodynamic diameter (MMAD) of the inhalable composite particles is between 2 µm and 4 µm when delivered from a dry powder inhaler; the inhalable composite particles are capable of providing an aerosol with an emitted dose (ED) of greater than or equal to about 70% when delivered from a dry powder inhaler; the composite particles are capable of providing an aerosol with an related standard deviation (RSD) of less than or equal to about 10% when determined on at least three samples delivered from a dry powder inhaler; the pharmaceutically-active agent within the provided composite particles has a median size of from about 50 nm to about 1000 nm.

In various aspects, the provided composite particles further comprise a milling aid; the millable grinding matrix is crystalline; the pharmaceutically-active agent is crystalline; the content uniformity of the solid pharmaceutically active agent dispersed in the composite particle varies from the average content by a percentage less than or equal to about 5.0%; the content uniformity of the pharmaceutically active agent throughout the blend has a percent relative standard deviation (RSD) less than or equal to about 5.0%; the inhalable composite particles have a roughness by surface area ratio greater than or equal to a ratio of about 1.1 (wherein the specific surface area is measured using nitrogen absorption and wherein the surface area is calculated from the spherical equivalent size determined by dry powder laser diffraction).

In various aspects: the composite particles have a Rrms greater than or equal to a height selected about 15 nm and wherein the Rrms is measured using atomic force microscopy; the composite particles have a Rrms greater than or equal to a height selected from about 15 nm and when the Rrms is measured using white light interferometry; the composite particles have a median of force adhesion (F[50]) less than or equal to about 150 nN when measured by atomic force microscopy; the weight of composite particles when dispensed from an automated or semi-automated filing machine deviates from the average weight dispensed by a percentage less than or equal to about 10%; the RSD from the average weight is less than or equal to about 10% when the number of samples measured is greater than or equal to 100 samples delivered from an automated or semi-automated filing machine; the step of providing composite particles comprises dry milling a composition comprising: a solid pharmaceutically active agent and a millable grinding matrix in a mill comprising a plurality of milling bodies for a time period sufficient to produce composite particles comprising grinding matrix and solid pharmaceutically active agent; the dry milling comprises milling in a mill with a plurality of milling bodies; the mill without milling bodies is selected from a cutter mill, end-runner mill, roller mill, hammer mill, fluid energy mill, pin mill, impact mill, mechanofusion mill, beater mill, jet mill and air jet mill.

In various aspects, the millable grinding matrix comprises one or more materials selected from an organic acid, organic base, polyol, peptide, protein, fat, fatty acid, amino acid (aspartic acid, glutamic acid, leucine, L-leucine, isoleucine, lysine, valine, methionine, phenylalanine, glycine, arginine, aspartic acid, glutamic acid, cysteine, alanine, serine, phenylalanine, lysine, N-acetyl-L-cysteine, or a pharmaceutically acceptable salt, solvate, hydrate, or polymorph thereof), carbohydrate (e.g., mannitol, sorbitol, xylitol, maltitol, lactitol, erythritol, arabitol, ribitol, glucose, fructose, mannose, galactose, lactose, sucrose, raffinose, ribitol, maltose, sorbose, cellobiose, sorbose, trehalose, maltodextrins, dextrans, inulin, 1-O-alpha-D-glucopyranosyl-D-mannitol (Isomalt)), or a pharmaceutically acceptable solvate, hydrate, or polymorph thereof, phospholipid, triglyceride, detergent, polymer, or a pharmaceutically acceptable salt, solvate, hydrate, or polymorph thereof.

In various aspects: the millable grinding matrix comprises lactose monohydrate and optionally one or more material selected from sodium chloride, anhydrous lactose, mannitol, glucose, sucrose, trehalose, sorbitol, 1-O-alpha-D-glucopyranosyl-D-mannitol (Isomalt), xylitol, maltitol, lactitol, erythritol, arabitol, ribitol, fructose, mannose, galactose, raffinose, ribitol, maltose, sorbose, cellobiose, sorbose, inulin, sodium citrate, sodium ascorbate. lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerols, phosphatidylinositol, phosphatidylserine, sodium lauryl sulphate, magnesium lauryl sulphate; PEG 6000, PEG 3000 Tween 80, Poloxamer 188, leucine, L-leucine, isoleucine, lysine, valine, methionine, phenylalanine, glycine, arginine, aspartic acid, glutamic acid, cysteine, alanine, and serine.

In various aspects: the composite particle further comprises a second pharmaceutically active agent, the method producing composite particles of the matrix having the solid pharmaceutically active agent and the second pharmaceutically active agent dispersed therein; the composite particles have a fine particle fraction ratio of the first pharmaceutically active agent and second pharmaceutically active agent less than or equal to about 1.2 when delivered from a dry powder inhaler and analyzed with a NGI with an induction port and a preseparator; the composite particles have a MMAD uniformity ratio of less than or equal to about 1.2 when delivered from a dry powder inhaler and analyzed with a NGI with an induction port and a preseparator, wherein the distribution of each of the first and second pharmaceutically active agent is assayed and each is used to calculate an MMAD for the composite particle.

Also described is an inhalable composition of pharmaceutically-active composite particles produced by any of the methods described above.

Also described is an inhalable pharmaceutically-active composition comprising: a plurality of composite particles comprising a millable grinding matrix and a solid pharmaceutically-active agent, wherein the composite particles of the grinding matrix and the pharmaceutically-active agent have a mass median aerodynamic diameter of from about 1 μm to about 20 μm; and wherein the pharmaceutically-active agent within the composite particles has an average particle size of from about 50 nm to about 3 μm.

In various aspects of this inhalable composition: the inhalable composite particles comprise a solid pharmaceutically-active agent having a median particle on a volume average basis between 50 nm and 3 μm; the inhalable composite particles have a median particle size on a volume average size less than or equal to 10,000 nm; the inhalable composite particles have a D90, determined on a particle volume basis, less than or equal to 15,000 nm; the inhalable composite particles have a D90, determined on a particle volume basis, greater than or equal to 2000 nm; the inhalable composite particles have a volume weighted mean (D4,3) less than or equal to 10,000 nm; the inhalable composite particles have a volume weighted mean (D4,3) greater than or equal to 1000 nm; the inhalable composite particles are capable of providing an aerosol with a mass median aerodynamic diameter (MMAD) of the inhalable composite particles between 1 nm and 10 nm when delivered from a dry powder inhaler; the inhalable composite particles are capable of providing an aerosol with a fine particle fraction (FPF) of emitted dose of the pharmaceutically active agent of greater than or equal to about 10% when delivered from a dry powder inhaler; the inhalable composite particles are capable of providing an aerosol with a related standard deviation (RSD) of the FPF of emitted dose of the pharmaceutically active agent of less than or equal to about 10%; the inhalable composite particles are capable of providing an aerosol with a fine particle fraction (FPF) of total recovered dose of the pharmaceutically active agent of greater than or equal to about 30% when delivered from a dry powder inhaler; the inhalable composite particles when delivered from a dry powder inhaler are capable of providing an aerosol with a mass median aerodynamic diameter (MMAD) of the inhalable composite particles from about 1 nm to about 10 nm and a FPF of the pharmaceutically active agent of at least about 10%; the inhalable composite particles are capable of providing an aerosol with a mass median aerodynamic diameter (MMAD) of the inhalable composite particles between 1 nm and 7 nm when delivered from a dry powder inhaler; the inhalable composite particles are capable of providing an aerosol with a mass median aerodynamic diameter (MMAD) of the inhalable composite particles between 1.5 nm and 5 nm when delivered from a dry powder inhaler; the inhalable composite particles are capable of providing an aerosol with a mass median aerodynamic diameter (MMAD) of the inhalable composite particles is between 2 nm and 5 nm when delivered from a dry powder inhaler; the inhalable composite particles are capable of providing an aerosol with a mass median aerodynamic diameter (MMAD) of the inhalable composite particles is between 2 nm and 4 nm when delivered from a dry powder inhaler; the inhalable composite particles are capable of providing an aerosol with an emitted dose (ED) of greater than or equal to about 70% when delivered from a dry powder inhaler; the composite particles are capable of providing an aerosol with an related standard deviation (RSD) of less than or equal to about 10% when determined on at least three samples delivered from a dry powder inhaler; the pharmaceutically-active agent within the provided composite particles has a median size of from about 50 nm to about 1000 nm; the provided composite particles further comprise a milling aid; the millable grinding matrix is crystalline; the pharmaceutically-active agent is crystalline; the content uniformity of the solid pharmaceutically active agent dispersed in the composite particle varies from the average content by a percentage less than or equal to about 5.0%; the content uniformity of the pharmaceutically active agent throughout the blend has a percent relative standard deviation (RSD) less than or equal to about 5.0%; the inhalable composite particles have a roughness by surface area ratio greater than or equal to a ratio of about 1.1 (wherein the specific surface area is measured using nitrogen absorption wherein the surface area is calculated from the spherical equivalent size determined by dry powder laser diffraction); the composite particles have a Rrms greater than or equal to a height selected about 15 nm and wherein the Rrms is measured using atomic force microscopy; the composite particles have a Rrms greater than or equal to a height selected from about 15 nm and when the Rrms is measured using white light interferometry; the composite particles have a median of force adhesion (F[50]) less than or equal to about 150 nN when measured by atomic force microscopy; the weight of composite particles when dispensed from an automated or semi-automated filing machine deviates from the average weight dispensed by a percentage less than or equal to about 10%; the RSD from the average weight is less than or equal to about 10% when the number of samples measured is greater than or equal to 100 samples delivered from an automated or semi-automated filing machine; the composite particle further comprises a second pharmaceutically active agent, the method producing composite particles of the matrix having the solid pharmaceutically active agent and the second pharmaceutically active agent dispersed therein; the composite particles have a fine particle fraction ratio of the first pharmaceutically active agent and second pharmaceutically active agent less than or equal to about 1.2 when delivered from a dry powder inhaler and analyzed with a NGI with an induction port and a preseparator; the composite particles have a MMAD uniformity ratio of less than or equal to about 1.2 when delivered from a dry powder inhaler and analyzed with a NGI with an induction port and a preseparator, wherein the distribution of each of the first and second pharmaceutically active agent is assayed and each is used to calculate an MMAD for the composite particle.

Also described is any of the forgoing pharmaceutical compositions formulated in a unit dosage form. In various aspects: the pharmaceutical composition comprises a gelatin capsule, the composition is suitable for use in a dry powder inhaler.

Also described is a dry powder inhaler comprising the pharmaceutical composition described above.

FIG. 1 shows representative SEM data of batch 4J (10,000× magnification).

FIG. 2 shows representative SEM data of batch 4J (100,000× magnification).

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Specific abbreviations used herein are as follows: "AFM" is an abbreviation for atomic force microscropy; "CI" is an abbreviation for Anderson Cascade Impactor; "MSLI" is an abbreviation for a Multi-Stage Liquid Impinger; and, "NGI" is an abbreviation for Next Generation Impactor.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound. A weight percent (wt. %) of a component, unless specifically stated to the contrary, is based on the total weight of the formulation or composition in which the component is included.

As used herein, the terms "administering" and "administration" refer to providing a pharmaceutical preparation to a subject by inhalation or nasal administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "blend" is refers to the resultant mixture of a pharmaceutically active agent and excipient particles combined together in a process that has the effect or intended effect of distributing the active and excipient particles in a uniform distribution throughout the final powder blend. In this definition the term excipient and matrix are interchangeable. An ensemble of composite particles as produced by the disclosed methods is one example of a blend. Typically, a blend is made using simple blending processes that do not involve granulation, but may involve a milling step.

As used herein, the term "carrier excipient" refers to a pharmaceutical excipient suitable for use in an orally inhaled formulation that may be combined with an inhalable composite particle to produce a formulation for therapeutic use.

As used herein, the term "carrier matrix" refers to all material that has been milled in with the pharmaceutically active agent and is now combined into a composite particle with nanoparticles of pharmaceutically active agent.

As used herein, the term "chemically-inert" refers to materials, e.g., milling bodies, that do not react chemically with the pharmaceutically active agent or the millable grinding matrix.

As used herein, the term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g., "Crystal Engineering of the Composition of Pharmaceutical Phases. Do Pharmaceutical Co-crystals Represent a New Path to Improved Medicines?" Almarasson, O., et al., *The Royal Society of Chemistry*, (2004), 1889-1896. Examples of co-crystals include p-toluenesulfonic acid and benzenesulfonic acid.

As used herein, the term "composite particle" refers to a particle comprising particles of a pharmaceutically active agent and particles of a millable grinding matrix (milled or partially milled) combined into a larger particle. In some case, the particles of pharmaceutically active agent and the particles of millable grinding matrix are dispersed in the composite particle. The composite particle can comprise particles of more than one pharmaceutically active agent or more than one millable grinding matrix. The composite particle can further comprise additional materials such as a milling aid. The particles of pharmaceutically active agent can be nanoparticles and/or microparticles, but are typically nanoparticles. The particles of millable grinding matrix can also be nanoparticles and/or microparticles.

As used herein, the term "content uniformity" refers to uniformity with which a pharmaceutically active agent is distributed throughout a blend. A blend with superior content uniformity will have the same concentration of pharmaceutically active agent in many samples taken from different places (e.g., top, middle and bottom) in a blend. Typically content uniformity is measured by assaying the sample by HPLC, or similar technique, to determine the concentration of active in a sample. Typically content uniformity is expressed as the percent (%) deviation of the many samples from the known concentration of the whole blend. In bulk powder samples, content uniformity may be measured from three or more samples. If the powder is filled into packaging such as a hard capsule or foil blister pack, then a number of packages will be assayed (typically 10 randomly chosen from a larger number) to determine the content uniformity. In the case where packages such as a capsule are assayed to determine the content uniformity of the powder, the assays should be corrected for the total weight of powder in each package. One common measure for content uniformity, is the percent deviation of each sample from average concentration or the known concentration of the whole blend. A specification then would be that no sample has a deviation greater than a certain percent. The second common measure is the relative standard deviation (RSD) of the sample assays from the average (either the average of the samples of the known concentration of the bulk powder).

As used herein, unless the context requires otherwise, the term "dry mill" or variations, such as "dry milling", refer to milling in at least the substantial absence of liquids. If liquids are present, they are present in such amounts that the contents of the mill retain the characteristics of a dry powder. In some cases dry milling takes place in the complete absence of liquid.

As used herein, the term "dry powder laser diffraction" refers to a laser diffraction measurement where compressed air is use to disperse a dry powder into an airstream that is passed through the measurement zone.

As used herein, the term "particle size" can refer to measurements made on individual particles or distributions of particles. The terms "particle size distribution," "average particle size," "median particle size," and "mean particle size" refer to the characterization of populations of particles which individually are not all of the same size, and are typically expressed in units of length (for example, nanometers or micrometers). These parameters can be measured by a variety of techniques including dynamic light scattering, static light scattering, laser diffraction, sedimentation, time of flight, or other methods known to those skilled in the art. Particle size distributions can also be quantified by a size that corresponds to a certain percentile of the distribution ($D_x$), wherein a certain percentage (x) of the population (on a volume, not weight basis) is smaller than the defined size. For example, a distribution having a $D_{90}$ value of 500 nm means that 90% of the distribution (on a volume basis) has a size that is less than 500 nm. As used herein, the terms "$D_{50}$" and "median particle size" are used interchangeably. The terms "average particle size" and "mean particle size" are used interchangeably and can be calculated from size distributions by methods known to those skilled in the art. Mean particle size can also be represented by the term "$D_{(4,3)}$" which refers to a method of calculating the mean of a distribution of particles.

As used herein, the term "effective aerodynamic size" refers to the characterization of a distribution of particles when measured in an air stream. The effective aerodynamic particle size may be represented in terms of a median, mean, average, or size corresponding to a specified percentile as determined by an aerodynamic measuring technique known to those skilled in the art.

As used herein, the terms "emitted dose" and "ED" are interchangeable, and refer to the fraction of the total dose available in the device delivered by an inhaler device. It is often expressed as a percentage.

As used herein, the terms "fine particle fraction" and "FPF" are interchangeable, and refer to the fraction of pharmaceutically active agent that has an aerodynamic diameter less than about 4-6 μm. Unless otherwise indicated, as used herein, FPF is determined using a NGI with induction port and preseparator. Other methods known to one skilled in the art to determine FPF include using a Multi-Stage Liquid Impinger (MSLI) with induction port or an Anderson Cascade Impactor (CI) with induction port and preseparator. FPF is expressed as a fraction of total dose, and typically it is expressed as a percentage of the total dose less than about 4-6 micron. Unless otherwise stated the FPF is the fraction relative to the emitted dose. Another definition is the FPF relative to the total recovered dose (TRD), and when this intended, it is indicated as FPF (TRD). The total recovered dose is the sum of emitted dose and the dose remaining in the device/dose packaging. It should be noted the disclosed composite particles comprise pharmaceutically active agent that is uniformly aggregated into the composite particles, thus the FPF is also an indicator of the fraction of composites with an aerodynamic diameter less than about 4-6 micron.

As used herein, the term "flowable" refers to a powder having physical characteristics rendering it suitable for further processing using typical equipment used for the manufacture of pharmaceutical compositions and formulations.

As used herein, the term "FPF uniformity ratio" refers to the ratio of two FPF values determined from the assay of two separate pharmaceutically active agents present in a single composite particle composition. The ratio is calculated by dividing the larger FPF with the smaller one. It should be noted that it only has meaning where there are two or more actives contained within a composite composition. If the FPF uniformity ratio is near 1 it is an indication that the two pharmaceutically active agents have a highly uniform distribution throughout the composite composition.

As used herein, the term "geometric standard deviation" or "GSD" are used interchangeable, and refers to the aerodynamice particle size distribution, and calculated as follows: $GSD=(d_{84}/d_{16})^{1/2}$. Unless otherwise indicated, as used herein, GSD is determined using a NGI with induction port and preseparator. Other methods known to one skilled in the art to determine GSD include using a MSLI with induction port or an CI with induction port and preseparator. As noted above for the definition of FPF, the disclosed composite particles comprise pharmaceutically active agent that is uniformly aggregated into the composite particles, thus although the GSD is determined from an assay of the active material it is a measurement of the aerodynamic size distribution of the composite particles.

As used herein, the phrase "identified to be in need of treatment for a disorder," or the like, refers to selection of a subject based upon need for treatment of the disorder. For example, a subject can be identified as having a need for treatment of a disorder (e.g., a respiratory disorder) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the phrase "inhalable composite" refers to a powder comprising composite particles that have the correct aerodynamic diameter to be orally inhaled into the lungs of a subject. The subject can be a human.

As used herein, the term "inhibit" refers to processes that includes prohibiting, preventing, restraining, and lowering, stopping, or reversing progression or severity, and such action on a resultant clinical or medical symptoms.

As used herein, the term "median force of adhesion" or "F[50]" both refer to the median force of adhesion between inhalable composite particles as measured by atomic force microscopy (AFM) where the median is taken from a large number (greater than 1000) of adhesion force measurements. Specifically, as used herein, F[50] is measured by atomic force microscopy using the methods as set forth by Adi et al. [*European Journal of Pharmaceutical Sciences,* 35 (2008) 12-18].

As used herein, the terms "mass median aerodynamic diameter" and "MMAD" are interchangeable, and refer to the aerodynamic diameter at which 50% of the particles by mass are larger and 50% are smaller. MMAD can be determined using a Next Generation Impactor (NGI) with induction port and preseparator. Other methods known to one skilled in the art to determine MMAD include using a Multi Stage Liquid Impinger (MSLI) with induction port or a Cascade Impactor (CI) with induction port and preseparator. MMAD can also be determined using time-of-flight measurements known to those skilled in the art. As noted above for the definition of FPF, the disclosed composite particles comprise pharmaceutically active agent that is uniformly aggregated into the composite particles, thus although the MMAD is determined from an assay of the active material it is a measurement of the aerodynamic size of the composite particles. MMAD is equivalent to the aerodynamic D50 value on a volume basis after correction for particle density.

As used herein, the term "MMAD uniformity ratio" refers to the ratio of two MMAD values determined from the assay of two separate pharmaceutically active agents present in a single composite particle composition. The ratio is calculated by dividing the larger MMAD with the smaller one. It should be noted that it only has meaning where there are two or more actives contained within a composite composition. If the MMAD uniformity ratio is near 1, then it is an indication that the two pharmaceutically active agents have a highly uniform distribution throughout the composite composition.

As used herein, the term "millable" refers to a millable grinding matrix that reduces in particle size under the dry milling conditions of the method of the invention.

As used herein, the term "millable grinding matrix" refers any inert substance that a pharmaceutically active agent can be or is combined with and milled to provide composite particles. The terms "co-grinding matrix" and "matrix" are interchangeable with "grinding matrix".

As used herein, the term "nanoparticle" refers to a particle having a size of about 1000 nm or less.

As used herein, the term "passive laser diffraction" refers to the process of measuring the size of a dry powder by using laser diffraction wherein the dry powder is dispered into an airstream that is pulled out of an inhalation device and through the measurement zone. The airflow pulled through the device is one that is within the normal range for human inhalation. Airflows would typically be, but not limited to a range of 20-100 liters/minute. Thus, the dry powder is mechanically dispersed by air being drawn out of the inhalation device and not by the particle size instrument.

As used herein, the term "pharmaceutically active agent" refers to any agent that when administered to a subject, has a therapeutic effect, a diagnostic effect, elicits a desired biological, and/or pharmacological effect. The term can be used interchangeably herein with "active", "active compound", and "biologically active". The pharmaceutically active agent can be used in the treatment, cure, prevention, or diagnosis of disease or used to otherwise enhance physical or mental well-being. As used herein, the term "roughness by surface area" refers to the ratio of the specific surface area (SSA) of the composite as measured by BET isotherm and the surface area calculated from laser diffraction particle size measurements of the composite wherein the laser diffraction measurement is by dry powder laser diffraction. The Roughness by Surface Area is a measure of the roughness of a particle, i.e., if the ratio of actual SSA to calculated surface area is high then the surface is rougher.

As used herein, the terms "roughness—root mean squared" and "Rrms" both refer to the square root of the mean squared where the mean squared is the sum of the square of the height (taken from the zero reference plane) divided by the number of data points. Specifically, as used herein, Rrms is measured by atomic force microscopy or scanning white light interferometry according to the methods set forth by Adi et al. [*Langmuir,* 24 (2008) 11307-11312].

As used herein, the term "segregation" refers to the stratification of the particle size distribution of a powder or blend. It can be caused by any physical process, but typically it occurs when a powder or blend undergoes flow or other movement. Examples of processes that can introduce segregation are, but not limited to, transport, blending and flow in a hopper or other processing equipment. A powder or blend in an unsegregated state will have an even distribution of particle sizes throughout the whole powder or blend such that any sample taken from any part of the bag or container holding the powder (such as top, middle, bottom) will give the same particle size distribution. In a powder that has undergone segregation some parts of the powder will have more large particles that other parts and some parts will have more small particles than other parts of the powder. In a powder with segregation samples taken from a variety of positions in the bag or container holding the powder (such as top, middle, bottom) will typically show some difference in the particle size distribution. In some cases, for testing of powder segregation, a method of forced segregation may be used in order to assess any changes to content uniformity after segregation. An example of forced segregation is to place the powder in a tube and rotate the tube at a slight angle for a long period such that large and small particles will separate.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

A. Preparation of Composite Particles

1. Composite Particles

In one aspect, the invention relates to composite particles comprising a millable grinding matrix and a pharmaceutically active agent. In a further aspect, the composite particles can further comprise a milling aid.

Without wishing to be bound by a particular theory, it is believed that the disclosed methods, at least in some cases, provide composite particles wherein the active particles are uniformly distributed or substantially uniformly distributed throughout the composite particles, so that each composite particle contains the same proportion of pharmaceutically active agent and millable grinding matrix. Thus, if segregation were to occur, the blend would retain superior content uniformity. In contrast, a conventional blend made with active particles smaller than the excipient particles would have poor content uniformity if the blend were to segregate.

Again, without wishing to be bound by a particular theory, it is believed that the pharmaceutically active agent is, at least in some cases, incorporated into a composite particle such that the majority of the exposed surface of the composite particle is the matrix material. As such the composite generally has the properties of the matrix material. As many active materials are cohesive in nature, this lowers interparticle interactions. In the case where the weight percent of pharmaceutically active agent is very low, the composite particle is composed almost entirely of the matrix material. In this case the influence of the active on particle particle interactions is almost completely eliminated. Thus, the formulation has only one type, or predominantly one type, of particle interaction. In conventional formulations, there are multiple particle-particle interactions which complicate the development of suitable formulations and the ability to use pharmaceutically active agents as desired.

A further benefit of the nature of composite particles provided by the disclosed methods is that if a carrier excipient is required in order to make a formulation suitable for therapeutic use, then a matrix such as lactose can be used in the dry milling step together with lactose as the carrier excipient. Thus, the particle particle interactions are simplified as they are with like materials.

Without wishing to be bound by a particular theory, it is believed that another beneficial property of the disclosed composite particles, at least in some cases, is improved powder flow, possibly arising from relative surface roughness that reduces surface contact and reduces cohesivity.

2. Method of Making an Inhalable Pharmaceutically-Active Composition

Described herein is a method for making inhalable composite particles comprising a pharmaceutically-active agent, the method comprising:
a) providing composite particles comprising a millable grinding matrix and a solid pharmaceutically-active agent, wherein the pharmaceutically-active agent has an median particle size on a volume average basis between 50 nm and 3 μm; and
b) milling the composite particles in a mill without milling bodies for a time period sufficient to produce inhalable composite particles having a mass median aerodynamic diameter between 1 μm and 20 μm.

In a further aspect, milling in a mill without milling bodies (in step b) is milling in a mill selected from a cutter mill, end-runner mill, roller mill, hammer mill, fluid energy mill, pin mill, impact mill, mechanofusion mill, beater mill, jet mill and air jet mill. In a still further aspect, milling in a mill without milling bodies is milling in an air jet mill. In a yet further aspect, the composite particles after air jet milling have an effective aerodynamic size from about 2 m to about 7 μm.

In a further aspect, the step of providing composite particles (step a) comprises the step of dry milling a mixture of: a solid pharmaceutically active agent, and a millable grinding matrix, in a mill comprising a plurality of milling bodies for a time period sufficient to produce composite particles of the grinding matrix having the solid pharmaceutically active agent with an effective aerodynamic size from about 1 μm to about 20 μm (e.g, 2 μm to 18 μm, 4 μm to 16μm, 6μm to 20 μm, 8 μm to 20 μm). In a yet further aspect, dry milling is milling in a mill with a plurality of milling bodies. In a still further aspect, the composite particles produced by dry milling have an effective aerodynamic size from about 5 μm to about 15 μm. In an even further aspect, the composite particles produced by dry milling have an effective aerodynamic size from about 10 μm to about 20 μm. In a still further aspect, the mixture that is dry milled further comprises a milling aid. In a yet further aspect, the mixture that is dry milled further comprises one or more milling aids. In a still further aspect, the mixture that is dry milled further comprises one or more pharmaceutically active agents.

In a further aspect, the method of making an inhalable pharmaceutically-active composition comprises the steps of: (a) dry milling a solid pharmaceutically active agent and a millable grinding matrix in a mill comprising a plurality of milling bodies, for a time period sufficient to produce nanoparticles of the pharmaceutically active agent dispersed in an at least partially milled grinding material; and, (b) milling the blend produced in step (a) in a mill without milling media to produce an inhalable composite particle comprising a pharmaceutically active agent and millable grinding matrix. In an even further aspect, the particles of pharmaceutically active agent dispersed in the composite particle are nanoparticles. In a yet further aspect, the mill used in the second step is an air jet mill. In a still further aspect, the pharmaceutically active agent has a median particle size less than or equal to about 1000 nm of a volume basis. In an even further aspect, the pharmaceutically active agent has a median particle size less than or equal to about 500 nm on a volume basis (e.g., a median size less than 400, 300, or 200 nm or has a $D_{50}$ is between 1000 and 500, between 600 and 300, between 500 and 200. In a still further aspect, the composite particle comprising a pharmaceutically active agent and millable grinding matrix have a composite particle size of less than or equal to about 10 μm. In a still further aspect, the composite particle comprising a pharmaceutically active agent and millable grinding matrix have a composite particle size of less than or equal to about 5 μm.

3. Dry Milling a. Milling Mixture

In one aspect, the invention relates to a method comprising dry milling a mixture comprising a solid pharmaceutically active agent and a millable grinding matrix. In a further aspect, the mixture further comprises one or more milling aids. In a still further aspect, a mixture further comprises a facilitating agent, wherein the facilitating agent is added to the mixture at a time prior to completion of the dry milling step.

In a further aspect, the millable grinding matrix is a single material or is a mixture of two or more materials in any proportion. In a still further aspect, the concentration of the single (or first) material is selected from 5-99.9%, 10-95%, 15-85%, 20-80%, 25-75%, 30-60%, and 40-50%, wherein the percent is given as a weight percent (w/w). In a yet further aspect, the concentration of the second or subsequent material is selected from 5-50%, 5-40%, 5-30%, 5-20%, 10-40%, 10-30%, 10-20%, 20-40%, and 20-30%, wherein the percent is given as a weight percent (w/w). In a yet further aspect, if the second or subsequent material, when present, is a surfactant, polymer, a lubricant or glidant the concentration is selected from 0.1-10%, 0.1-5%, 0.1-2.5%, 0.1-2%, 0.1-1%, 0.5-5%, 0.5-3%, 0.5-2%, 0.5-1.5%, 0.5-1%, 0.75-1.25%, 0.75-1% and 1%, wherein the percent is given as a weight percent (w/w).

In a further aspect, the milling aid, when present, is in a concentration selected from 0.1-10%, 0.1-5%, 0.1-2.5%. 0.1-2%, 0.1-1%, 0.5-5%, 0.5-3%, 0.5-2%, 0.5-1.5%, 0.5-1%, 0.75-1.25%, 0.75-1%, and 1%, wherein the percent is given as a weight percent (w/w).

b. Milling Apparatus

In one aspect, the dry milling apparatus is a mill comprising a plurality of milling bodies. In a further aspect, the mill comprising a plurality of milling bodies is selected from a ball mill, sand mill, bead mill, pearl mills, basket mill, planetary mill, vibratory action ball mill, multi-axial shaker/mixer, stirred ball mill, horizontal small media mill, and multi-ring pulverizing mill. In a yet further aspect, the mill comprising a plurality of milling bodies is selected from an attritor mill, nutating mill, tower mill, planetary mill, vibratory mill and gravity-dependent-type ball mill. In a still further aspect, the mill comprising a plurality of milling bodies is a ball mill. In a yet further aspect, the milling media within the milling apparatus is mechanically agitated by 1, 2 or 3 rotating shafts. In a still further aspect, the dry milling operation is configured to produce the nanoparticles of pharmaceutically active agent in a continuous fashion.

In a further aspect, the dry milling is carried out in a mill selected from attritor mills (horizontal or vertical), nutating mills, tower mills, pearl mills, planetary mills, vibratory mills, eccentric vibratory mills, gravity-dependent-type ball mills, rod mills, and crusher mills.

c. Processing Time

In one aspect, dry milling has a milling time period in the range selected from between 10 minutes and 2 hours, between 10 minutes and 90 minutes, between 10 minutes and 1 hour, between 10 minutes and 45 minutes, between 10 minutes and 30 minutes, between 5 minutes and 30 minutes, between 5 minutes and 20 minutes, between 2 minutes and 10 minutes, between 2 minutes and 5 minutes, between 1 minutes and 20 minutes, between 1 minute and 10 minutes, and between 1 minute and 5 minutes.

In a further aspect, dry milling of the pharmaceutically active agent and the millable grinding matrix is for the shortest time necessary to form the composite particle comprising the pharmaceutically active agent and the millable grinding matrix. In a still further aspect, dry milling of the pharmaceutically active agent and the millable grinding matrix is for a time such that contamination from the media mill and/or the plurality of milling bodies is minimized. The time varies greatly, depending on the pharmaceutically active agent and the millable grinding matrix, and may range from as short as one minute to several hours. In a still further aspect, dry milling times in excess of two hours can lead to degradation of the pharmaceutically active agent and an increased level of undesirable contaminants.

In a further aspect the total milling times are adjusted for the type and size of milling apparatus as well as the milling media, the weight ratio of the pharmaceutically active agent and millable grinding matrix mixture to the plurality of milling bodies, the chemical and physical properties of the pharmaceutically active agent and grinding matrix, and other parameters that can be optimized empirically by one skilled in the art.

d. Milling Bodies

In one aspect, the dry mill with a plurality of milling bodies uses milling media fabricated from a material selected from ceramics, glasses, polymers, ferromagnetics and metals. In a further aspect, the milling media is steel balls having a diameter selected from between 1 mm and 20 mm, between 2 mm and 15 mm and between 3 mm and 10 mm. In a yet further aspect, the milling medium is zirconium oxide balls having a diameter selected from between 1 mm and 20 mm, between 2 mm and 15 mm and between 3 mm and 10 mm. In an even further aspect, the milling bodies are steel balls having a diameter selected from about between 1mm and 20 mm. In a still further aspect, the milling bodies have a density of about 1 g/cm$^3$ to about 15 g/cm$^3$. In a yet further aspect, the milling bodies have a density of about preferably from about 1 g/cm$^3$ to about 8 g/cm$^3$.

In a further aspect, the milling bodies are chemically inert and rigid. In a still further aspect, the milling bodies are essentially resistant to fracture and erosion in the milling process. In a yet further aspect, the milling bodies are provided in the form of bodies which can have any of a variety of smooth, regular shapes, flat or curved surfaces, and lacking sharp or raised edges. For example, suitable milling bodies can be in the form of bodies having ellipsoidal, ovoid, spherical or right cylindrical shapes. In an even further aspect, the milling bodies are provided in the form of one or more of beads, balls, spheres, rods, right cylinders, drums or radius-end right cylinders (i.e., right cylinders having hemispherical bases with the same radius as the cylinder).

The milling bodies can comprise various substances such as ceramic, glass, metal or polymeric compositions, in a particulate form. Suitable metal milling bodies are typically spherical and generally have good hardness (i.e., RHC 60-70), roundness, high wear resistance, and narrow size distribution and can include. In a further aspect, metal materials can be selected from type AISI52100 chrome steel, type 316 or 440C stainless steel or type AISI1065 high carbon steel. Suitable ceramic milling bodies, for example, can be selected from a wide array of ceramics desirably having sufficient hardness and resistance to fracture to enable them to avoid being chipped or crushed during milling and also having sufficiently high density. In a further aspect, ceramic materials can be selected from steatite, aluminum oxide, zirconium oxide, zirconia-silica, yttria-stabilized zirconium oxide, magnesia-stabilized zirconium oxide, silicon nitride, silicon carbide, cobalt-stabilized tungsten carbide, and the like, as well as mixtures thereof. In a further aspect, glass milling bodies are spherical (e.g., beads), have a narrow size distribution, are durable, and include, for example, lead-free soda lime glass and borosilicate glass. In a still further aspect, polymeric milling media are substantially spherical and can be selected from a wide array of polymeric resins having sufficient hardness and friability to enable them to avoid being chipped or crushed during milling, abrasion-resistance to minimize attrition resulting in contamination of the product, and freedom from impurities such as metals, solvents, and residual monomers. In a yet further aspct, polymeric resins can be selected from crosslinked polystyrenes, such as polystyrene crosslinked with divinylbenzene, styrene copolymers, polyacrylates such as polymethylmethacrylate, polycarbonates, polyacetals, vinyl chloride polymers and copolymers, polyurethanes, polyamides, high density polyethylenes, polypropylenes, and the like. The use of polymeric milling media to grind materials down to a very small particle size (as opposed to mechanochemical synthesis) is disclosed, for example, in U.S. Pat. Nos. 5,478,705 and 5,500,331. In a further aspect, polymeric resins have densities ranging from about 0.8 g/cm$^3$ to about 3.0 g/cm$^3$. Alternatively, the milling media can be composite particles comprising dense core particles having a polymeric resin adhered thereon. Core particles can be selected from substances known to be useful as milling media, for example, glass, alumina, zirconia silica, zirconium oxide, stainless steel, and the like. In a further aspect, core substances have densities greater than about 2.5 g/cm$^3$. In a still further aspect, the milling media are formed from a ferromagnetic substance, thereby facilitating removal of contaminants arising from wear of the milling media by the use of magnetic separation techniques.

Each type of milling body has its own advantages. For example, metals have the highest specific gravities, which increase grinding efficiency due to increased impact energy. Metal costs range from low to high, but metal contamination of final product can be an issue. Glasses are advantageous from the standpoint of low cost and the availability of small bead sizes as low as 0.004 mm. However, the specific gravity of glasses is lower than other media and significantly more milling time is required. Finally, ceramics are advantageous from the standpoint of low wear and contamination, ease of cleaning, and high hardness.

e. Milling Conditions

In one aspect, the total combined amount of pharmaceutically active agent and millable grinding matrix in the mill at any given time is greater than or equal to a mass selected from about 200 g, 500 g, 1 kg, 2 kg, 5 kg, 10 kg, 20 kg, 30 kg, 50 kg, 75 kg, 100 kg, 150 kg, and 200 kg. In a further aspect, the total combined amount of pharmaceutically active agent and grinding matrix in the mill at any given time is less than about 2000 kg.

4. Milling in a Mill without Milling Bodies

In one aspect, the invention relates to a milling step comprising milling in a mill without milling bodies. In a further aspect, composite particles are provided and milling is carried out on the composite particles in a mill without milling bodies. In a yet further aspect, composite particles have been prepared by dry milling in a first step, and the composite particles are further milled in a second step in a mill a without milling bodies. In a still further aspect, the mill without milling bodies is selected from cutter mills, end-runner mills, roller mills, hammer mills, fluid energy mills, impact mill, mechanofusion mill, beater mill, jet mill and air jet mills.

In a further aspect, the sub-particles of pharmaceutically-active agent within the composite particles, after milling in a mill without milling bodies, have an average particle size of from about 50 nm to about 3 μm.

In a further aspect, the composite particles after milling in a mill without milling bodies have a median particle size less than or equal to about 10,000 nm. In a still further aspect, the composite particles after milling in a mill without milling bodies have a D90, determined on a particle volume basis, less than or equal to about 15,000 nm. In a yet further aspect, the composite particles after milling in a mill without milling bodies have a D90, determined on a particle volume basis, greater than or equal to about 2000 nm. In an even further aspect, the composite particles after milling in a mill without milling bodies have a volume weighted mean (D4,3) less than or equal to about 10,000 nm. In a yet further aspect, the composite particles after milling in a mill without milling bodies have a volume weighted mean (D4,3) greater than or equal to about 1000 nm.

In a further aspect, the mill without milling bodies is an air jet mill. In a still further aspect, the air jet mill is a size selected from 2 inch, 4 inch, 8 inch, 10 inch, 15 inch, 20 inch, 30 inch and 42 inch. In a yet further aspect, the air pressure in the air jet mill is selected from 1 bar, 2 bar, 3 bar, 4 bar, 5 bar, 6 bar, 7 bar, 8 bar, 9 bar and 10 bar. In an even further aspect, the powder feed rate into the air jet mill is selected from 0.5 kg/hr, 1.0 kg/hr, 5 kg/hr, 10 kg/hr, 15 kg/hr, 20 kg/hr, 35 kg/hr, 50 kg/hr, 75 kg/hr, 100 kg/hr, 150 kg/hr, 200 kg/hr, 500 kg/hr and 1000 kg/hr.

In a further aspect, a facilitating agent is added to the composite particles produced at the end of milling in a mill without milling bodies, and then further processed in another milling device such as a mechanofusion mill, cyclomixing device, or impact mill. The impact mill for the further processing is selected from a ball mill and a jet mill. Alternatively, in a further aspect, the further processing is carried out a high pressure homogenizer. In a still further aspect, the further processing is carried out using a combination of two or more of mechanofusion mill, cyclomixing device, impact mill, or high pressure homogenizer.

B. Materials Used in Preparation of Composite Particles

1. Millable Grinding Matrix

In one aspect, the invention relates to a millable grinding matrix used in the preparation of a composite particle comprising a pharmaceutically active agent and the millable grinding matrix. In a further aspect, the millable grinding matrix is of a comparable particle size to the pharmaceutically active agent. In a still further aspect, the particle size of the millable grinding matrix is substantially reduced but not as small as the pharmaceutically active agent material. In a yet further aspect, the millable grinding matrix is selected from the group consisting of: a material considered to be Generally Regarded as Safe (GRAS) for inhaled pharmaceutical products or a material considered acceptable for use in a veterinary formulation. In an even further aspect, millable grinding matrix can be either an inorganic or organic substance.

In a further aspect, the millable grinding matrix comprises one or more materials selected from an organic acid, organic base, sugar, polyol, peptide, protein, fat, fatty acid, amino acid, carbohydrate, phospholipid, triglyceride, detergent, polymer, or a pharmaceutically acceptable salt, solvate, hydrate, or polymorph thereof. In a still further aspect, the millable grinding matrix is sodium chloride.

In a further aspect, the millable grinding matrix is a carbohydrate selected from mannitol, sorbitol, xylitol, maltitol, lactitol, erythritol, arabitol, ribitol, glucose, fructose, mannose, galactose, lactose, sucrose, raffinose, ribitol, maltose, sorbose, cellobiose, sorbose, trehalose, maltodextrins, dextrans, inulin, 1-O-alpha-D-glucopyranosyl-D-mannitol (Isomalt), or a pharmaceutically acceptable solvate, hydrate, or polymorph thereof.

In a further aspect, the millable grinding matrix is an amino acid selected from aspartic acid, glutamic acid, leucine, isoleucine, lysine, valine, methionine, phenylalanine, glycine, arginine, aspartic acid, glutamic acid, cysteine, alanine, serine, phenylalanine, lysine, wherein the amino acid can be either the D configuration, the L configuration or the DL configuration as appropriate to the end use. N-acetyl-L-cysteine, or a pharmaceutically acceptable salt, solvate, hydrate, or polymorph thereof.

In a further aspect, the millable grinding matrix is a phospholipid selected from dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerol, phosphatidylinositol, phosphatidylserine, or a pharmaceutically acceptable solvate, hydrate, or polymorph thereof.

In a further aspect, the millable grinding matrix is a fatty acid selected from palmitic acid, stearic acid, erucic acid, behenic acid, lauric acid, or a pharmaceutically acceptable salt, solvate, hydrate, or polymorph thereof. In a yet further aspect, the fatty acid is a salt selected from sodium stearyl fumarate, sodium stearyl lactylate, zinc stearate, magnesium stearate, calcium stearate, sodium stearate, lithium stearate, sodium lauryl sulphate, magnesium lauryl sulphate, or a pharmaceutically acceptable solvate, hydrate, or polymorph thereof.

In a further aspect, the millable grinding matrix is a salt of an organic acid selected from sodium gluconate, magnesium gluconate, sodium citrate, sodium ascorbate. In a still further aspect, the millable grinding matrix is human serum albumin. In a yet further aspect, the millable grinding matrix is a fat selected from lecithin and soy lecithin. In an even further aspect, the millable grinding matrix is selected from Dynsan 118, Cutina HR, gelatine, hypromellose, polyethylene glycol, PEG 6000, PEG 3000, PEGS, Tween 80, and Poloxamer 188.

In a further aspect, the millable grinding matrix comprises lactose monohydrate and optionally one or more material selected from sodium chloride, anhydrous lactose, mannitol, glucose, sucrose, trehalose, sorbitol, 1-O-alpha-D-glucopyranosyl-D-mannitol (Isomalt), xylitol, maltitol, lactitol, erythritol, arabitol, ribitol, fructose, mannose, galactose, raffinose, ribitol, maltose, sorbose, cellobiose, sorbose, inulin, sodium citrate, sodium ascorbate, lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerols, phosphatidylinositol, phosphatidylserine, sodium lauryl sulphate, magnesium lauryl sulphate, PEG 6000, PEG 3000 Tween 80, Poloxamer 188, leucine, isoleucine, lysine, valine, methionine, phenylalanine, glycine, arginine, aspartic acid, glutamic acid, cysteine, alanine, and serine, wherein the amino acid can be the D configuration, the L configuration, or the DL configuration as appropriate to the desired application.

In a further aspect, the millable grinding matrix comprises lactose anhydrous and optionally one or more material selected from sodium chloride, lactose monohydrate, mannitol, glucose, sucrose, trehalose, sorbitol, 1-O-alpha-D-glucopyranosyl-D-mannitol (Isomalt), xylitol, maltitol, lactitol, erythritol, arabitol, ribitol, fructose, mannose, galactose, raffinose, ribitol, maltose, sorbose, cellobiose, sorbose, inulin, sodium citrate, sodium ascorbate, lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerols, phosphatidylinositol, phosphatidylserine, sodium lauryl sulphate, magnesium lauryl sulphate, PEG 6000, PEG 3000 Tween 80, Poloxamer 188, leucine, isoleucine, lysine, valine, methionine, phenylalanine, glycine, arginine, aspartic acid, glutamic acid, cysteine, alanine, and serine, wherein the amino acid can be the D configuration, the L configuration, or the DL configuration as appropriate to the desired application.

In a further aspect, the millable grinding matrix comprises mannitol and optionally one or more material selected from sodium chloride, lactose monohydrate, lactose anhydrous, glucose, sucrose, trehalose, sorbitol, 1-O-alpha-D-glucopyranosyl-D-mannitol (Isomalt), xylitol, maltitol, lactitol, erythritol, arabitol, ribitol, fructose, mannose, galactose, raffinose, ribitol, maltose, sorbose, cellobiose, sorbose, inulin, sodium citrate, sodium ascorbate. lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerols, phosphatidylinositol, phosphatidylserine, sodium lauryl sulphate, magnesium lauryl sulphate; PEG 6000, PEG 3000 Tween 80, Poloxamer 188, leucine, isoleucine, lysine, valine, methionine, phenylalanine, glycine, arginine, aspartic acid, glutamic acid, cysteine, alanine, and serine, wherein the amino acid can be the D configuration, the L configuration, or the DL configuration as appropriate to the desired application.

In a further aspect, the millable grinding matrix comprises sucrose and optionally one or more material selected from sodium chloride, lactose monohydrate, lactose anhydrous, mannitol, glucose, trehalose, sorbitol, 1-O-alpha-D-glucopyranosyl-D-mannitol (Isomalt), xylitol, maltitol, lactitol, erythritol, arabitol, ribitol, fructose, mannose, galactose, raffinose, ribitol, maltose, sorbose, cellobiose, sorbose, inulin, sodium citrate, sodium ascorbate, lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerols, phosphatidylinositol, phosphatidylserine, sodium lauryl sulphate, magnesium lauryl sulphate, PEG 6000, PEG 3000 Tween 80, Poloxamer 188, leucine, isoleucine, lysine, valine, methionine, phenylalanine, glycine, arginine, aspartic acid, glutamic acid, cysteine, alanine, and serine, wherein the amino acid can be the D configuration, the L configuration, or the DL configuration as appropriate to the desired application.

In a further aspect, the millable grinding matrix comprises glucose and optionally one or more material selected from sodium chloride, lactose monohydrate, lactose anhydrouse, mannitol, sucrose, trehalose, sorbitol, 1-O-alpha-D-glucopyranosyl-D-mannitol (Isomalt), xylitol, maltitol, lactitol, erythritol, arabitol, ribitol, fructose, mannose, galactose, raffinose, ribitol, maltose, sorbose, cellobiose, sorbose, inulin, sodium citrate, sodium ascorbate, lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerols, phosphatidylinositol, phosphatidylserine, sodium lauryl sulphate, magnesium lauryl sulphate, PEG 6000, PEG 3000 Tween 80, Poloxamer 188, leucine, isoleucine, lysine, valine, methionine, phenylalanine, glycine, arginine, aspartic acid, glutamic acid, cysteine, alanine, and serine, wherein the amino acid can be the D configuration, the L configuration, or the DL configuration as appropriate to the desired application.

In a further aspect, the millable grinding matrix comprises sodium chloride and optionally one or more material selected from lactose anhydrous, lactose monohydrate, mannitol, glucose, sucrose, trehalose, sorbitol, 1-O-alpha-D-glucopyranosyl-D-mannitol (Isomalt), xylitol, maltitol, lactitol, erythritol, arabitol, ribitol, fructose, mannose, galactose, raffinose, ribitol, maltose, sorbose, cellobiose, sorbose, inulin, sodium citrate, sodium ascorbate, lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerols, phosphatidylinositol, phosphatidylserine, sodium lauryl sulphate, magnesium lauryl sulphate, PEG 6000, PEG 3000 Tween 80, Poloxamer 188, leucine, isoleucine, lysine, valine, methionine, phenylalanine, glycine, arginine, aspartic acid, glutamic acid, cysteine, alanine, and serine, wherein the amino acid can be the D configuration, the L configuration, or the DL configuration as appropriate to the desired application.

In a further aspect, the millable grinding matrix comprises trehalose and optionally one or more material selected from sodium chloride, lactose anhydrous, lactose monohydrate, mannitol, glucose, sucrose, sorbitol, 1-O-alpha-D-glucopyranosyl-D-mannitol (Isomalt), xylitol, maltitol, lactitol, erythritol, arabitol, ribitol, fructose, mannose, galactose, raffinose, ribitol, maltose, sorbose, cellobiose, sorbose, inulin, sodium citrate, sodium ascorbate, lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerols, phosphatidylinositol, phosphatidylserine, sodium lauryl sulphate, magnesium lauryl sulphate, PEG 6000, PEG 3000 Tween 80, Poloxamer 188, leucine, L-leucine, isoleucine, lysine, valine, methionine, phenylalanine, glycine, arginine, aspartic acid, glutamic acid, cysteine, alanine, and serine, wherein the amino acid can be the D configuration, the L configuration, or the DL configuration as appropriate to the desired application.

In a further aspect, the millable grinding matrix is a single material or is a mixture of two or more materials in any proportion. In a still further aspect, the material is selected from sodium chloride, mannitol, sorbitol, Isomalt, xylitol, maltitol, lactitol, erythritol, arabitol, ribitol, glucose, fructose, mannose, galactose, anhydrous lactose, lactose monohydrate, sucrose, raffinose, ribitol, maltose, sorbose, cellobiose, sorbose, trehalose, Inulin, Isomalt other sugars or polyols, aspartic acid, glutamic acid, sodium gluconate, maltodextrins, dextrans, magnesium gluconate, peptides and proteins such as human serum albumin, organic salts such as sodium citrate and sodium ascorbate lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerols, phosphatidylinositol, phosphatidylserine or other phospholipids; stearic acid and derivatives or salts thereof such as sodium stearyl fumarate, sodium stearyl lactylate, zinc stearate, magnesium stearate, calcium stearate, sodium stearate, lithium stearate; solid state fatty acids such as, palmitic acid, stearic acid, erucic acid, behenic acid, or derivatives therof, including esters and salts; lauric acid and its salts, for example, sodium lauryl sulphate, magnesium lauryl sulphate; triglycerides such as Dynsan 118 and Cutina HR; gelatine, hypromellose; PEG 6000, PEG 3000 or other PEGS; Tween 80, Poloxamer 188; amino acids, such as aspartic acid, glutamic acid, leucine, L-leucine, isoleucine, lysine, valine, methionine, phenylalanine, glycine, arginine, aspartic acid, glutamic acid, cysteine, alanine, serine, phenyl alanine lysine, N-acetyl-L-cysteine, wherein the amino acid can be the D configuration, the L configuration, or the DL configuration as appropriate to the desired appalication, and derivatives, salts, solvates, hydrates, and polymorphs thereof; and, peptides and polypeptides having molecular weight from 0.25 kDa to 1000 kDa.

In one aspect, the millable grinding matrix is selected from: lactose (e.g., lactose monohydrate), mannitol, glucose, sucrose, and xylitol.

In a further aspect, the grinding matrix is harder than pharmaceutically active agent, and is thus capable of reducing the particle size of the active material under dry milling conditions. Without wishing to be bound by particular theory, under the disclosed dry milling conditions it is believed that the millable grinding matrix affords the advantage of the smaller particles of grinding matrix produced under the dry milling conditions enabling greater interaction with the pharmaceutically active agent. It is also believed, without wishing to be bound by a particular theory, that the physical degradation (including but not limited to particle size reduction) of the millable grinding matrix affords the advantage of acting as a more effective diluent than grinding matrix of a larger particle size.

In a further aspect, the quantity of the grinding matrix relative to the quantity of pharmaceutically active agent, and the extent of physical degradation of the grinding matrix, is sufficient to inhibit re-agglomeration of the particles of the active material. In a still further aspect, the quantity of the grinding matrix relative to the quantity of pharmaceutically active agent, and the extent of physical degradation of the grinding matrix, is sufficient to inhibit re-agglomeration of the particles of the active material in nanoparticulate form. In a further aspect, the grinding matrix is not generally selected to be chemically reactive with the pharmaceutically active agent under the disclosed milling conditions, excepting for example, where the matrix is deliberately chosen to undergo a mechanico-chemical reaction, e.g., the conversion of a free base or acid to a salt or vice versa. Without wishing to be bound by a particular theory, the grinding matrix the grinding matrix will physically degrade under the disclosed dry milling conditions to facilitate the formation and retention of particulates of the pharmaceutically active agent with reduced particle size. The precise extent of degradation required will depend on certain properties of the grinding matrix and the pharmaceutically active agent, the ratio of pharmaceutically active agent to grinding matrix, and the particle size distribution of the particles comprising the pharmaceutically active agent.

The physical properties of the grinding matrix necessary to achieve the requisite degradation are dependent on the precise milling conditions. For example, a harder grinding matrix may degrade to a sufficient extent provided it is subjected to more vigorous dry milling conditions. Physical properties of the grinding matrix relevant to the extent that the agent will degrade under dry milling conditions include hardness, friability, as measured by indicia such as hardness, fracture toughness and brittleness index. A low hardness (typically a Mohs Hardness less than 7) of the pharmaceutically active agent is desirable to ensure fracture of the particles during processing, so that composite microstructures develop during milling. Preferably, the hardness is less than 3, as determined using the Mohs Hardness scale.

In a further aspect, the grinding matrix is of low abrasivity. Without wishing to be bound by a particular theory, low abrasivity is desirable to minimize contamination of the mixture of the pharmaceutically active agent in the grinding matrix by the milling bodies and/or the milling chamber of the media mill. An indirect indication of the abrasivity can be obtained by measuring the level of milling-based contaminants.

In a further aspect, the millable grinding matrix has a low tendency to agglomerate during dry milling. While it is difficult to objectively quantify the tendency to agglomerate during milling, it is possible to obtain a subjective measure by observing the level of "caking" of the grinding matrix on the milling bodies and the milling chamber of the media mill as dry milling progresses.

2. Milling Aid

In one aspect, the invention relates to the use of a milling aid in the disclosed methods to prepare the composite particles comprising a pharmaceutically active agent and a millable grinding matrix. In a further aspect, the composite particle further comprises a milling aid. In a yet further aspect, a milling aid or combination of milling aids is used in the dry milling step. In a further aspect, the milling aid is added to mixture of pharmaceutically active agent and millable grinding matrix at a time prior to the completion of the dry milling step. In a yet further aspect, the milling aid is added at a time prior to the completion of milling in a mill without milling bodies.

In a further aspect, the milling aid is selected from surfactants, polymers, phospholipids, fatty acids or derivatives, stearic acid and derivatives thereof, and amino acids or derivatives.

In a further aspect, the milling aid is selected from lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerols, phosphatidylinositol, phosphatidylserine sodium stearyl fumarate, sodium stearyl lactylate, zinc stearate, magnesium stearate, calcium stearate, sodium stearate, lithium stearate, palmitic acid, stearic acid, erucic acid, behenic acid, sodium lauryl sulphate, magnesium lauryl sulphate; Dynsan 118, Cutina HR, aspartic acid, gelatine, glutamic acid, hypromellose, PEG 6000, PEG 3000, Tween 80, Poloxamer 188, leucine, L-leucine, isoleucine, lysine, valine, methionine, phenylalanine, glycine, arginine, aspartic acid, glutamic acid, cysteine, alanine, serine, phenyl alanine lysine and N-acetyl-L-cysteine.

In a further aspect, the milling aid is selected from lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, phosphatidylethanolamine, phosphatidylglycerols, phosphatidylinositol, phosphatidylserine or other phospholipids, sodium stearyl fumarate, sodium stearyl lactylate, zinc stearate, magnesium stearate, calcium stearate, sodium stearate, lithium stearate. solid state fatty acids such as, palmitic acid, stearic acid, erucic acid, behenic acid, or derivatives (such as esters and salts) thereof, lauric acid and its salts, for example, sodium lauryl sulphate, magnesium lauryl sulphate; triglycerides such as Dynsan 118 and Cutina HR, aspartic acid, gelatine, glutamic acid, hypromellose, PEG 6000, PEG 3000 or other PEGS, Tween 80, Poloxamer 188, amino acids, such as leucine, isoleucine, lysine, valine, methionine, phenylalanine, glycine, arginine, aspartic acid, glutamic acid, cysteine, alanine, serine, phenyl alanine lysine, and derivatives, wherein the amino acid can be the D configuration, the L configuration, or the DL configuration as appropriate to the desired application, thereof, N-acetyl-L-cysteine, and peptides and polypeptides having molecular weight from 0.25 to 1000 kDa.

In one aspect the milling aid is selected from: lecithin, phospholipids, polyvinylpyrrolidone, polyoxyethylene sorbate esters, polysorbate 80, polysorbate 20.

In one aspect the millable grinding matrix is selected from: lactose (e.g., lactose monohydrate), mannitol, glucose, sucrose, and xylitol.

In one aspect the millable grinding matrix is selected from: lactose (e.g., lactose monohydrate), mannitol, glucose, sucrose, and xylitol and the milling aid is selected from: lecithin, phospholipids, polyvinylpyrrolidone, polyoxyethylene sorbate esters, polysorbate 80, polysorbate 20.

3. Facilitating Aid

In a further aspect, the facilitating agent is selected from one or more of lecithin; soy lecithin, dipalmitoyl phosphatidylcholine, phosphatidylglycerol, dipalmitoyl phosphatidyl ethanolamine, dipalmitoyl phosphatidylinositol, phospatidylcholine, phosphatidylethanolamine, phosphatidylglycerol, phosphatidylinositol, phosphatidylserine, phospholipid, sodium stearyl fumarate, sodium stearyl lactylate, zinc stearate, magnesium stearate, calcium stearate, sodium stearate, and lithium stearate.

In a further aspect, the facilitating agent is selected from a solid state fatty acids. In yet further aspect, the solid state fatty acid is selected from palmitic acid, stearic acid, erucic acid, and behenic acid, or derivatives thereof such as esters and salts. In a still further aspect, the facilitating agent is selected from lauric acid and a lauric acid salt. In an even further aspect, the lauric acid salt is selected from sodium lauryl sulphate and magnesium lauryl sulphate. In a still further aspect, the facilitating agent is a triglyceride. In a yet further aspect, the triglyceride is selected from Dynsan 118 and Cutina HR.

In a further aspect, the facilitating agent is an amino acid. In yet further aspect, the amino acid is selected from aspartic acid, glutamic acid, leucine, isoleucine, lysine, valine, methionine, phenylalanine, glycine, arginine, aspartic acid, glutamic acid, cysteine, alanine, serine, N-acetyl-cysteine, phenylalanine, lysine, or pharmaceutically acceptable derivatives, salts, solvates, hydrates, and polymorphs thereof.

In a further aspect, the facilitating agent is selected from peptides and polypeptides having molecular weight from 0.25 to 1000 KDa. In a yet further aspect, the facilitating agent is selected from gelatine, hypromellose, PEG 6000, PEG 3000 or other PEGS, Tween 80, and Poloxamer 188.

4. Pharmaceutically Active Agent

In one aspect, the invention relates to a pharmaceutically active agent selected from vitamins, pharmaceutical actives, biologics, amino acids, proteins, peptides, polypeptides, nucleotides, oligonucleotides, vaccines, monoclonal antibodies, nucleic acids, or a pharmaceutically acceptable salt, derivative, solvate, hydrate, or polymorph thereof. In a further aspect, pharmaceutically active agent is agent used in the treatment of a disorder in an animal. In a still further aspect, the pharmaceutically active agent is used in the treatment of a disorder in human.

In a further aspect, the pharmaceutically active agent is an organic compound. In a still further aspect, the pharmaceutically active agent is a material for which one of skill in the art desires to deliver to the lung by oral inhalation. In a yet further aspect, the pharmaceutically active agent can also be a material for which one of skill in the art desires improved dissolution properties. Examples of pharmaceutically active agents are provided below (Additional Embodiments).

C. Nanoparticles of Pharmaceutically Active Agent

1. Methods for Determining Particle Size of the Pharmaceutically Active Agent

There are a wide range of techniques that can be utilized to characterize the particle size distribution of a material. The technique that is chosen to characterize a material will depend on the size of the material to be analysed, the information required and the nature of the material to be sized. If the particles to be measured are less than 1 µm, it will be difficult to use any aerodynamic or dry powder measurement system. Instead other common ensemble methods must be used. As the active particles in this invention are typically less than 1 µm such techniques are required. Amongst these various methods, two types of measurements are most commonly used. Photon correlation spectroscopy (PCS), also known as 'dynamic light scattering' (DLS) is commonly used to measure particles with a size less than 10 micron. Typically this measurement yields an equivalent hydrodynamic radius often expressed as the average size of a number distribution. The other common particle size measurement is laser diffraction, which is commonly used to measure particle size from 100 nm to 2000 µm. This technique calculates a volume distribution of equivalent spherical particles that can be expressed using descriptors such as the median particle size or the percent of particles under a given size.

Those skilled in the art also understand that almost all these techniques do not physically measure the actually particle size, as one might measure something with a ruler, but measure a physical phenomena which is interpreted to indicate a particle size. As part of the interpretation process some assumptions need to be made to enable mathematical calculations to be made. These assumptions deliver results such as an equivalent spherical particle size, or a hydrodynamic radius.

Those skilled in the art recognize that different characterization techniques such as photon correlation spectroscopy and laser diffraction measure different properties of a particle ensemble. As a result multiple techniques will give multiple answers to the question, "what is the particle size." In theory, one could convert and compare the various parameters each technique measures, however, for real world particle systems this is not practical. As a result the particle size used to describe this invention can be given as two different sets of values that each relate to these two common measurement techniques, such that measurements could be made with either technique and then evaluated against the description of this invention.

For measurements made using a photo correlation spectroscopy instrument, or an equivalent method known in the art, the term "number average particle size" is defined as the average particle diameter as determined on a number basis.

For measurements made using a laser diffraction instrument, or an equivalent method known in the art, the term "median particle size" is defined as the median particle diameter as determined on an equivalent spherical particle volume basis. Where the term median is used, it is understood to describe the particle size that divides the population in half such that 50% of the population is greater than or less than this size. The median particle size is often written as D50, D(0.50) or D[0.5] or similar. As used herein D50, D(0.50) or D[0.5] or similar shall be taken to mean 'median particle size'.

The term "Dx of the particle size distribution" refers to the xth percentile of the distribution on a particle volume basis; thus, D90 refers to the 90th percentile, D95 refers to the 95th percentile, and so forth. Taking D90 as an example this can often be written as, D(0.90) or D[0.9] or similar. With respect to the median particle size and Dx an upper case D or lowercase d are interchangeable and have the same meaning. Another way to quantitate a particle size distribution is the volume weighted mean (D4,3). D4,3 is defined as sum of the diameters to the power 4 divided by the sum of the diameters cubed.

Another commonly used way of describing a particle size distribution measured by laser diffraction, or an equivalent method known in the art, is to describe what % of a distribution is under or over a nominated size. The term "percentage less than" also written as "%<" is defined as the percentage, by volume, of a particle size distribution under a nominated size—for example the %<1000 nm. The term "percentage greater than" also written as "%>" is defined as the percentage, by volume, of a particle size distribution over a nominated size—for example the %>1000 nm.

The particle size used to describe this invention should be taken to mean the particle size as measured at or shortly before the time of use. For example, the particle size is measured 2 months after the material is subject to the milling method of this invention. In a preferred form, the particle size is measured at a time selected from the group consisting of: 1 day after milling, 2 days after milling, 5 days after milling, 1 month after milling, 2 months after milling, 3 months after milling, 4 months after milling, 5 months after milling, 6 months after milling, 1 year after milling, 2 years after milling, 5 years after milling.

For many of the materials subject to the methods of this invention the particle size can be easily measured. Where the active material has poor water solubility and the matrix it is milled in has good water solubility the powder can simply be dispersed in an aqueous solvent. In this scenario the matrix dissolves leaving the active material dispersed in the solvent. This suspension can then be measured by techniques such as PCS or laser diffraction.

Suitable methods to measure an accurate particle size where the active material has substantive aqueous solubility or the matrix has low solubility in a water based dispersant, are outlined below.

In the circumstance where insoluble matrix such as microcrystalline cellulose prevents the measurement of the active material, separation techniques such as filtration or centrifugation could be used to separate the insoluble matrix from the active material particles. Other ancillary techniques would also be required to determine if any active material was removed by the separation technique, so that this could be taken into account.

In the case where the active material is too soluble in water, other solvents could be evaluated for the measurement of particle size. Where a solvent could be found that active material is poorly soluble in, but is a good solvent for the matrix, a measurement would be relatively straight forward. If such a solvent is difficult to find, another approach would be to measure the ensemble of matrix and active material in a solvent (such as iso-octane) which both are insoluble in. Then the powder would be measured in another solvent where the active material is soluble, but the matrix is not. Thus with a measurement of the matrix particle size and a measurement of the size of the matrix and active material together, an understanding of the active material particle size can be obtained. Another approach to measuring actives particles with moderate to high aqueous solubility, is to measure the size in a saturated solution of the active material.

In some circumstances image analysis could be used to obtain information about the particle size distribution of the active material. Suitable image measurement techniques might include transmission electron microscopy (TEM), scanning electron microscopy (SEM), optical microscopy and confocal microscopy. In addition to these standard techniques some additional technique would be required to be used in parallel to differentiate the active material and matrix particles. Depending on the chemical makeup of the materials involved possible techniques could be elemental analysis, Raman spectroscopy, FTIR spectroscopy or fluorescence spectroscopy.

In some other cases nanoparticles of pharmaceutically active agents are formed, but have small amounts of agglomeration or bridging present. Thus when they are analyzed by an ensemble technique such as laser diffraction they appear to be much larger particles. As those skilled in the pharmaceutical arts would understand, the key to such materials is not what size an instrument may indicate, but product performance. So, if the particles are indeed nano sized in dimension and have high surface area that is available, then they will perform as nanoparticles in vivo.

In this invention, the key aspect required of the pharmaceutically active agent is that it is small enough to be uniformly distributed throughout the composite material, even after the composite particle size has been reduced to an inhalable size. So where ensemble particle size methods such as laser diffraction cannot be used, other techniques and numerics will be required to characterize the material. Some examples of these methods are, but not limited to:

1. Image analysis of SEM micrographs of the composites;
2. SEM or TEM microscopy combined with elemental or spectrographic analysis;
3. SEM or TEM microscopy optionally combined with elemental or spectrographic analysis on slices of composite particles prepared in a resin;
4. AFM analysis combined with Raman microscopy;
5. Image analysis of SEM micrographs of the active materials after the matrix material has been washed out; and,
6. Specific surface area (SSA) measurements of the active material after the matrix material has been washed out. From the SSA an equivalent spherical diameter could be calculated or the SSA itself could be used as a quantitative descriptor. There would be a requirement to dry the active material after washing out the matrix. It is important to preserve the high surface area during the washing and drying process. One possible way to do this would be to spray dry the active material.

2. Pharmaceutically Active Agent Particle Size

In one aspect, the invention relates to a composite particle comprising a millable grinding matrix and a pharmaceutically active agent wherein the pharmaceutically active is a particle dispersed in the composite particle. In a further aspect, the sub-particles of pharmaceutically active agent within the composite particles are nanoparticles. In a still further aspect, sub-particles of pharmaceutically active agent within the composite particles produced by the disclosed methods have particle size of less than or equal to 1000 nm. In a yet further aspect, sub-particles of pharmaceutically active agent within the composite particles produced by the disclosed methods have particle size of less than or equal to 500 nm. In an even further aspect, the sub-particles of pharmaceutically-active agent are crystalline. In a further aspect, the sub-particles of pharmaceutically-active agent within the composite particles have an average particle size of from about 50 nm to about 1000 nm.

In a further aspect, the sub-particles of the pharmaceutically active agent within the composite particles have a median particle size, determined on a particle volume basis, less than or equal to a size selected from about 1000 nm, 900 nm, 800 nm, 700 nm, 600 nm, 500 nm, 400 nm, 300 nm, 200 nm and 100 nm. In a yet further aspect, the median particle size of the pharmaceutically active agent is greater than or equal to about 25 nm.

In a further aspect, the percentage of particles of the pharmaceutically active agent, on aparticle volume basis, is selected from 50%, 60%, 70%, 80%, 90%, 95% and 100%, wherein the percentage represents the fraction less than about 1000 nm, 800 nm, 600 nm, 400 nm or 200 nm or between 1000 nm and 500 nm, 900 nm and 400 nm, 800 nm and 300 nm. In a still further aspect, the percentage of particles of the pharmaceutically active agent, on a particle volume basis, is selected from 50%, 60%, 70%, 80%, 90%, 95% and 100%, wherein the percentage represents volume basis is less than about 500 nm. In a yet further aspect, the percentage of particles of the pharmaceutically active agent, on a particle volume basis, is selected from 50%, 60%, 70%, 80%, 90%, 95% and 100%, wherein the percentage represents the fraction less than about 300 nm. In an even further aspect, the percentage of particles of the pharmaceutically active agent, on a particle volume basis, is selected from 50%, 60%, 70%, 80%, 90%, 95% and 100%, wherein the percentage represents the fraction less than about 200 nm.

In a further aspect, the Dx (e.g., $D_{50}$) of the particle size distribution of the pharmaceutically active agent, as measured on a particle volume basis, is selected from 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm, and 100 nm; wherein x is greater than or equal to about 90.

3. Dissolution Profile

The disclosed methods result in the pharmaceutically active agent having an improved dissolution profile. An improved dissolution can provide improved bioavailability of the pharmaceutically active agent in vivo. In one aspect, the improved dissolution profile is observed in vitro. In a further aspect, the improved dissolution profile is observed in vivo by the observation of an improved bioavailability profile. Standard methods for determining the dissolution profile of a material in vitro are available in the art. A suitable method to determine an improved dissolution profile in vitro can include determining the concentration of the sample material in a solution over a period of time and comparing the results from the sample material to a control sample. An observation that peak solution concentration for the sample material was achieved in less time than the control sample can indicate that the sample material has an improved dissolution profile if results meet statistical significance.

Typically, all of the formulation is placed into the dissolution apparatus for testing when measuring a typical dissolution profile. Such a procedure is used when assessing the dissolution profile of an oral formulation. In the case of an oral medication this is appropriate, as all of the active in the formulation is taken into the gastro-intestinal tract, where it has an opportunity to be absorbed by the body. In contrast, not all of the active particles of an inhaled formulation can effectively reach the lung, where the active material can be either act locally or be absorbed systemically. In order to make a more precise estimation of what an in vivo dissolution profile may be from an in vitro measurement, the formulation must first be separated into those components that will reach the lung and those that will not. Only those components that are likely to reach the lung should be assessed. Son et al. [*Dissolution Technologies*, 17(2), 6-13 (2010)], herebye incorporated by reference, have demonstrated such a method. By actuating an inhaled formulation through a NGI device fitted with extra filters they were able to collect the fraction of particles that had a MMAD suitable for deposition in the lung. This fraction of the particles was then tested in a standard dissolution apparatus.

In a further aspect, the dissolution profile of the disclosed composite particles, inhalable composites, or inhalable compositions can be determined as described above and compared to a conventional inhalable composition. A conventional formulation is defined as an inhaled formulation that have been made using jet milled active and a carrier excipient such as lactose.

Standard methods for determining the improved dissolution profile of a material in vivo are available in the art. A suitable method to determine an improved dissolution profile in a human may be after delivering the dose to measure the rate of active material absorption by measuring the plasma concentration of the sample compound over a period of time and comparing the results from the sample compound to a control. An observation that peak plasma concentration for the sample compound was achieved in less time than the control would indicate (assuming it is statistically significant) that the sample compound has improved bioavailability and an improved dissolution profile. Preferably, the improved dissolution profile is observed in a dissolution medium that is similar to fluids found in the lung, when it is observed in vitro. Suitable methods for quantifying the concentration of a compound in an in vitro sample or an in vivo sample are widely available in the art. Suitable methods could include the use of spectroscopy or radioisotope labeling.

D. Composite Particle Characteristics

1. Particle Size of the Composite Particle a. Methods for Determining

One measurement that can be used to characterise the particle size of the composites is the aerodynamic particle size. As used herein aerodynamic particle size refers to a volume or mass particle size measurement which is based on the aerodynamic characteristics of the particles being measured. It is known to those skilled in the art that the aerodynamic diameter D(a) of an individual particle is related to its density (ρ) and Stokes diameter D(s) according to the equation: $D(a)=D(s)(\rho)^{1/2}$. The Stokes diameter of a particle is the diameter of a sphere which has the same terminal settling velocity as the particle being measured. Thus, the aerodynamic size of a particle is a measure of how it behaves when aerosolized. Aerodynamic particle size can be measured with commercially available instruments such as the Aerosizer LD or Model 3321 Aerodynamic Particle Sizer® (TSI Incorporated, Shoreview, Minn. 55126 USA) or similar instruments known to those skilled in the art.

Another measurement that can be used to determine the size of the composites is laser diffraction. These measurements can be broadly divided into wet methods and dry methods. Wet methods use a solvent such as iso-octane or isopar G which will not dissolve the matrix and for almost all pharmaceutical actives will not dissolve the active either. The composites are first dispersed in the solvent, sometimes with dispersion aids such as lecithin, and then measured using a standard wet laser diffraction measurement cell. Laser diffraction instruments to conduct these measurements are well known in the art, some examples of which are Malvern Mastersizers, Sympatec and Microtrac. Dry powder laser diffraction measurements use the same principle as wet methods only in this case an air stream is used to disperse and carry the particles through the laser beam. Examples of measurement instruments that do this are the Scirocco measurement cell for use with a Malvern Mastersizer, a Turbotrac dispersion unit with a Microtrac instrument or a RODOS dispersion unit used with a Sympatec laser diffraction instrument. In these measurement instruments, compressed air is used to disperse the powder so that the primary particle size of the composite can be measured.

Another approach to dry powder laser diffraction measurements is to use passive dispersion method. When these measurements are performed there is no dispersion cell in the instrument itself. Instead, the powder is packaged into an inhalation device that is attached to the measurement instrument. A defined airflow is then pulled through the instrument causing the powder to exit the device (after any dispersion the device may impart) and pass through the laser beam. The airflows used in passive laser diffraction are typically in the range of 20-100 L/min. Airflows in this range are used as they mimic the airflows during human inhalation. That is, pulling air through the device and dispersing the powder in a similar way to that which occurs when a patient uses the device, means the powder properties are also similar to what will happen during patient use. In this way a particle size distribution of the powder dispersed is obtained that is similar to that which is inhaled by a patient. Laser diffraction instruments to conduct passive laser diffraction measurements are well known in the art, some examples of which are the Malvern Spraytec or a Sympatec instrument with an INHALER module.

All three laser diffraction techniques, wet, dry powder and passive, measure the same physical property: a diffraction pattern created by the ensemble of particles within the measurement zone. The instrument then calculates a particle size distribution (by volume or mass) of equivalent spherical particle size. The particle size distributions would typically be characterised by the median particle size (D[50]), the volume weighted mean (D[4,3]) or the $90^{th}$ percentile (D[90]).

Another approach to the measurement of aerodynamic particle size is to use devices that measure aerodynamic particle size directly, by means of flow through different sized gratings. Examples of such devices are impactors and impingers where particles will be retained at multiple stages depending on their aerodynamic size. Particles smaller that any given stage will continue to further stages until a stage is reached where the size is larger than the cutoff. An assay can then be used to establish mass balances across a series of stages with different size cutoffs to establish the particle size distribution. Typically the assay is of the active material present in the formulation. In a conventional inhalation formulation the active particles are discrete particles so the assay and subsequent particle size distribution is of the actives particles from a formulation that have made their way into the testing device. In contrast, the disclosed composite particles have the pharmaceutically active agent particles uniformly distributed throughout the composite particles so in effect they are a marker probe that enables the mass distribution of the composite particle throughout the impactor or impinger stages to be determined. Thus the aerodynamic particle size distribution calculated is effectively of the composite particles in the formulation. Examples of impactors and impingers are the CI, MSLI and the NGI.

It is important to note that these measurement devices do not measure the aerodynamic particle size of the entire ensemble of particles (such as happens in a time of flight instrument such as the Aerosizer LD or Model 3321 Aerodynamic Particle Sizer®). This is because before the powder enters the impactor/impinger it must first travel through an induction port (often referred to as a throat) and in some devices a preseparator which will both remove some of the powder from the airstream. By design the induction port and preseparator remove larger particles from a distribution. This means the measurement does not report the size distribution of the entire powder sample, but rather the aerodynamic particle size of the material which passes through the induction port and preseparator. These impactors/impingers are designed this way in order to mimic what happens when a dry powder formulation is orally inhaled. In the oral inhalation process large particles will have larger momentum and will hit the back of the throat while those particles in the correct size range will flow down into the lungs. For this reason, measurements from impactors/impingers provide the best in vitro indication of in vivo performance.

It is still necessary and important to know and measure the particle size distribution of the whole powder as this provides knowledge of the potential for the powder formulation once coupled with an inhalation device. Measurements such as laser diffraction and time of flight measurements are easier and are therefore useful in providing tools for optimization and fast quality control analysis. From this information provided by the mass distribution across the various stages of an impactor/impinger the following can be determined: a Mass Median Aerodynamic Diameter (MMAD), a geometric standard deviation (GSD) and the FPF. These parameters are described in greater detail below.

b. Composite Particle Characteristics

In one aspect, the invention relates to composite particles comprising millable grinding matrix and a pharmaceutically active agent with appropriate particle size properties. In a further aspect, the disclosed composite particles of a millable grinding matrix and a pharmaceutically active agent have a median particle size of about 1 μm to about 20 μm. In a yet further aspect, the disclosed composite particles comprising millable grinding matrix and a pharmaceutically active agent have a median particle size less than or equal to about 10 μm. In a still further aspect, the disclosed composite particles comprising millable grinding matrix and a pharmaceutically active agent have a median particle size less than or equal to about 5 μm. In an even further aspect, the disclosed composite particles comprising millable grinding matrix and a pharmaceutically active agent have a median particle size less than or equal to about 4 μm. In a yet further aspect, the disclosed composite particles comprising millable grinding matrix and a pharmaceutically active agent have a particle size less than or equal to about 3 μm.

In a further aspect, the composite particles have a median particle size less than or equal to about 10,000 nm. In a still further aspect, the composite particles have a D90, determined on a particle volume basis, less than or equal to about 15,000 nm. In a yet further aspect, the composite particles have a D90, determined on a particle volume basis, greater than or equal to about 2000 nm. In an even further aspect, the composite particles have a volume weighted mean (D4,3) less than or equal to about 10,000 nm. In a still further aspect, the composite particles have a volume weighted mean (D4,3) greater than or equal to about 1000 nm.

In a further aspect, the composite particles comprising millable grinding matrix and a pharmaceutically active agent have a median particle size, determined on a particle volume basis, less than or equal to a size selected from 10,000 nm, 8000 nm, 6000 nm, 5000 nm, 4500 nm, 4000 nm, 3500 nm, 32500 nm, 3000 nm, 2900 nm, 2800 nm, 2700 nm, 2600 nm, 2500 nm, 2400 nm, 2300 nm, 2200 nm, 2100 nm, 2000 nm, 1900 nm, 1800 nm, 1700 nm, 1600 nm and 1500 nm. In a yet further aspect, the composite particles comprising millable grinding matrix and a pharmaceutically active agent have a median particle size is greater than or equal to 1000 nm. In a yet further aspect, the median particle size is measured by dry powder laser diffraction, passive dry powder laser diffraction or wet laser diffraction. In an even further aspect, the median particle size is measured by passive laser diffraction.

In a further aspect, the composite particles comprising millable grinding matrix and a pharmaceutically active agent have a volume weighted mean (D4,3) less than or equal to a size selected from 10,000 nm, 8000 nm, 6000 nm, 5000 nm, 4500 nm, 4000 nm, 3500 nm, 3250 nm, 3000 nm, 2900 nm, 2800 nm, 2700 nm, 2600 nm, 2500 nm, 2400 nm, 2300 nm, 2200 nm, 2100 nm, 2000 nm, 1900 nm, 1800 nm, 1700 nm, 1600 nm and 1500 nm. In a yet further aspect, the composite particles comprising millable grinding matrix and a pharmaceutically active agent have a volume weighted mean (D4,3) greater than or equal to about 1000 nm. In an even further aspect, the (D4,3) is measured by dry powder laser diffraction, passive dry powder laser diffraction or wet laser diffraction. In an even further aspect, the (D4,3) is measured by passive laser diffraction.

In a further aspect, the composite particles comprising millable grinding matrix and a pharmaceutically active agent have a D90, determined on a particle volume basis, less than or equal to a size selected from 15,000 nm, 12,000 nm, 11,000 nm, 10,000 nm, 9000 nm, 8000 nm, 7000 nm, 6000 nm, 5000 nm, 4000 nm and 3000 nm. In a yet further aspect, the composite particles comprising millable grinding matrix and a pharmaceutically active agent have a D90 is greater than or equal to about 2000 nm. In a still further aspect, the D90 is measured by dry powder laser diffraction, passive dry powder laser diffraction or wet laser diffraction. In a still further aspect, the D90 is measured by pass laser diffraction.

In a further aspect, the composite particles comprising millable grinding matrix and a pharmaceutically active agent have a mean particle size less than or equal to a size selected from 15,000 nm, 12,000 nm, 11,000 nm, 10,000 nm, 9000 nm, 8000 nm, 7000 nm, 6000 nm, 5000 nm, 4000 nm and 3000 nm. In a yet further aspect, the composite particles comprising millable grinding matrix and a pharmaceutically active agent have mean particle size greater than or equal to about 1000 nm. In a still further aspect, the mean particle size is measured by a time-of-flight instrument.

2. Content Uniformity a. Methods for Determining

Content uniformity in the present context is a measure of how evenly the pharmaceutically active agent(s) are distributed throughout a blend. Content uniformity is vital for accurate delivery of the pharmaceutically active agent to the lungs in a dry powder formulation. However, in some current commercial formulations as little as 0.02 mg of pharmaceutically active agent in 5 mg dose of powder is delivered to the lungs from an inhalation device. For optimal therapeutic and clinical value, content uniformity in powder for inhalation must be very accurate and highly repeatable.

Typically content uniformity is measured by assaying a number of samples by HPLC or similar technique to determine the concentration of pharmaceutically active agent in each sample. In bulk powder samples, content uniformity can be measured from three or more samples. If the powder is filled into packaging such as a hard capsule or foil blister pack then an appropriate number of packages will be assayed to determine the content uniformity (e.g., typically 10 randomly chosen from a larger number). In the case where packages such as a capsule are assayed to determine the content uniformity of the material, the assays should be corrected for the total weight of powder in each package. One common measure for content uniformity is the percent deviation of each sample from the average concentration or known concentration of the blend (e.g., batch or lot). For quality control, a content uniformity specification would provide that no sample has a deviation greater than a defined percentage. The second common measure is the RSD of the sample assays from the average (e.g., RSD from the average of the samples analyzed, or alternatively, the RSD from the known or nominal concentration of the bulk material).

The term "segregation" refers to the stratification of the particle size distribution of a material such as a powder or blend. It can be caused by any physical process, but typically it occurs when a powder or blend undergoes flow or other movement, e.g., during shipment, handling, storage, and blending and flow in a hopper or other processing equipment. A powder or blend in an unsegregated state will have an even distribution of particle sizes throughout the whole powder or blend such that any sample taken from any part of the bag or container holding the powder (such as top, middle, bottom) will give the same particle size distribution. In a powder that has undergone segregation some parts of the powder will have more large particles that other parts and some parts will have more small particles than other parts of the powder. In a powder with segregation samples taken from a variety of positions in the bag or container holding the powder (such as top, middle, bottom) will typically show some difference in the particle size distribution. For testing a powder's properties, forced segregation may be used in order to assess any changes to content uniformity after segregation. An example of forced segregation would be to place the powder in a tube and rotate the tube at a slight angle for a long period such that large and small particles will separate.

b. Composite Particle Characteristics

In one aspect, the invention relates to composite particles comprising millable grinding matrix and a pharmaceutically active agent with appropriate content uniformity properties. In a further aspect, the content uniformity of the solid pharmaceutically active agent dispersed in the composite particle varies from the average content by a percentage less than or equal to about 5.0%. In a yet further aspect, the content uniformity of the pharmaceutically active agent throughout the blend varies from the average content by a percentage less than or equal to a percentage selected from 0.1%, 0.2%, 0.3%, 0.4%, 0.5%, 0.75%, 1.0%, 1.5%, 2.0%, 3.0%, 4.0% and 5.0%. In a still further aspect, the content uniformity after segregation of the pharmaceutically active agent throughout the blend varies from the average content by a percentage less than or equal to a percentage selected from 0.1%, 0.2%, 0.3%, 0.4%, 0.5%, 0.75%, 1.0%, 1.5%, 2.0%, 3.0%, 4.0% and 5.0%. In a yet further aspect, the content uniformity of the pharmaceutically active agent throughout the blend has a RSD less than or equal to a percentage selected from 0.1%, 0.2%, 0.3%, 0.4%, 0.5%, 0.75%, 1.0%, 1.5%, 2.0%, 3.0%, 4.0% and 5.0%. In a still further aspect, the content uniformity of the pharmaceutically active agent throughout the blend has a percent relative standard deviation (RSD) less than or equal to about 5.0%. In an even further aspect, the content uniformity after segregation of the pharmaceutically active agent throughout the blend has a RSD less than or equal to a percentage selected from 0.1%, 0.2%, 0.3%, 0.4%, 0.5%, 0.75%, 1.0%, 1.5%, 2.0%, 3.0%, 4.0% and 5.0%.

3. Surface Roughness a. Methods for Determining

The shape, texture and roughness of individual particles and their distribution for an assembly of particles is an important particle property that affects several critical properties of particles used inhalation compositions, including flowability, cohesiveness, and dissolution properties. In one aspect, the surface roughness can be characterized by parameters such as Roughness by Surface Area (RSA), Roughness—root mean square (Rrms), and median force of adhesion (F[50]). The meaning and use of these terms is described above. Briefly, RSA can be determined by measurement of the specific surface area (SSA) using nitrogen absorption, with the BET isotherm and the surface area calculated from the spherical equivalent size determined by laser diffraction. In a further aspect, the laser diffraction method used is powder laser diffraction. Both Rrms and F[50] can be measured using atomic force microscopy per the methodology set forth by Adi, et al. (*Langmuir*, 2008, 34:11307-11312 and *Pharm. Sci.*, 2008, 35:12-18, respectively). Rrms can also be measured using scanning white light interferometry as described by Adi et al. (*Langmuir, ibid*).

b. Composite Particle Characteristics

In one aspect, the invention relates to composite particles comprising millable grinding matrix and a pharmaceutically active agent with appropriate surface roughness properties. In a further aspect, the composite particles have a roughness by surface area ratio greater than or equal to a ratio of about 1.1; wherein the specific surface area is measured using nitrogen absorption; and, wherein the surface area is calculated from the spherical equivalent size determined by dry powder laser diffraction. In a still further aspect, the composite particles have a Rrms greater than or equal to a height selected about 15 nm and wherein the Rrms is measured using atomic force microscopy. In a yet further aspect, the composite particles have a Rrms greater than or equal to a height selected from about 15 nm and wherein the Rrma is measured using white light interferometry. In an even further aspect, the composite particles have a median of force adhesion (F[50]) less than or equal to about 150 nN when measure by atomic force microscopy.

In a further aspect, the composite particles comprising millable grinding matrix and a pharmaceutically active agent have a Rrms greater than or equal to a height selected from 15 nm, 30 nm, 50 nm, 75 nm, 100 nm, 125 nm, 150 nm, 175 nm, 200 nm, 225 nm, 250 nm, 275 nm, 300 nm, 325 nm, 350 nm, 375 nm and 400 nm. In a yet further aspect, the composite particles comprising millable grinding matrix and a pharmaceutically active agent have a roughness by surface area ratio greater than or equal to a ratio selected from 1.1, 1.2, 1.3, 1.4, 1.5, 1.75, 2.0, 2.25, 2.5, 2.75, 3.0, 3.25, 3.5, 3.75, 4, 4.5 and 5.0. In a still further aspect, the composite particles comprising millable grinding matrix and a pharmaceutically active agent have a F[50] less than or equal to a force selected from 150 nN, 125 nN, 100 nN, 80 nN, 70 nN, 60 nN, 50 nN, 40 nN, 30 nN, 25 nN, 20 nN, 15 nN, 10 nN and 5 nN.

4. Cohesivity and Powder Flow a. Methods for Determining

In order to produce a commercially viable dry powder formulation, the powder flow must be suitable for accurate and precise delivery of small amount of powder. The amount of powder typically delivered in an inhaled dry powder inhaler is typically in the range of about 1 to about 20 mg. For formulations with high loadings this amount can be higher, e.g., about 20 to about 200 mg. The powder comprising the pharmaceutically active agent and carrier excipients must have flow properties that enable accurate and precise delivery of a fixed amount of powder. Depending upon the type of device used to deliver the powder the method used to measure this accuracy and precision will differ. If the powder is delivered in a reservoir style device the device itself will be used to deliver an aliquot amount of powder for each inhalation. In other devices some sort of packaging is used to pre-fill a single dose into an appropriate container for actuation in the device. Examples of such packaging are hard gelatine capsules, hard HMPC capsules, foil blister strips or foil blister rings. Filling of such packaging is carried out using an automated or semi automated dispenser to fill the capsules or foil blisters. The accuracy and precision that such a dispenser can deliver a given dose of powder is a measure of the powder flow, i.e., good powder flow results in better accuracy and repeatability. In contrast, poor powder flow results in variability in the amount of powder delivered to the capsule or foil blister. The variability of powder dispensed from an automated or semi automated filling machine could be quantified in a number of ways. For example, the weight of several samples dispensed into packaging can be determined, and then the percentage that each sample weight varies from the average weight delivered is calculated. Alternatively, the variability of powder dispensed can be determined from measuring the weight of several samples dispensed into packaging and calculate the variation in weight in terms of the RSD of a number of samples from the average weight delivered.

b. Composite Particle Characteristics

In one aspect, the invention relates to composite particles comprising millable grinding matrix and a pharmaceutically active agent with appropriate properties of cohesivity and powder flow. In a further aspect, the weight of composite particles when dispensed from an automated or semi-automated filling machine deviates from the average weight dispensed by a percentage less than or equal to about 10%. In a still further aspect, the relative standard deviation (RSD) from the average weight is less than or equal to about 10% when the number of samples measured is greater than or equal to 50 samples delivered from an automated or semi-automated.

In a further aspect, the weight dispensed from an automated filling machine of a powder comprising composite particles deviates from the average weight dispensed by a percentage less than or equal to a percentage selected from 0.1%, 0.2%, 0.3%, 0.4%, 0.5%, 0.75%, 1.0%, 1.5%, 2.0%, 3.0%, 4.0%, 5.0%, 6.0%, 7.0%, 8.0%, 9.0% and 10.0%, wherein the composite particles comprise a millable grinding matrix and a pharmaceutically active agent. In a still further aspect, for such testing the target weight of a powder comprising composite particles to be dispensed is selected from 1 mg, 2 mg, 5 mg, 10 mg, 15 mg, 20 mg, 25 mg, 30 mg, 40 mg, 50 mg, 75 mg, 100 mg, 150 mg and 200 mg. In a yet further aspect, for such testing the number of dispensed samples to be weighed is selected from 3, 5, 10, 15, 20, 25, 30, 50, and 100. In an even further aspect, a semi-automated filling machine is used to dispense the powder instead of an automated filling machine.

In a further aspect, the weight dispensed from an automated filling machine of a powder comprising composite particles has a RSD from the average weight dispensed is a percentage less than or equal to a percentage selected from 0.1%, 0.2%, 0.3%, 0.4%, 0.5%, 0.75%, 1.0%, 1.5%, 2.0%, 3.0%, 4.0%, 5.0%, 6.0%, 7.0%, 8.0%, 9.0% and 10.0%, wherein the composite particles comprise a millable grinding matrix and a pharmaceutically active agent. In a still further aspect, for such testing the target weight of a powder comprising composite particles to be dispensed is selected from 1 mg, 2 mg, 5 mg, 10 mg, 15 mg, 20 mg, 25 mg, 30 mg, 40 mg, 50 mg, 75 mg, 100 mg, 150 mg and 200 mg. For such a test the number of dispensed samples to be weighed is selected from the group consisting of: 3, 5, 10, 15, 20, 25, 30, 50, 100. In a yet further aspect, for such testing the number of dispensed samples to be weighed is selected from 3, 5, 10, 15, 20, 25, 30, 50, and 100. In an even further aspect, a semi-automated filling machine is used to dispense the powder instead of an automated filling machine.

5. Stability a. Methods for Determining

A critical characteristic of a dry powder inhalation formulation, is the stability of the formulation performance over time during storage. Typically, parameters such as as the emitted dose (ED), FPF and MMAD are determined as a function of time. These parameters need to be relatively stable over a reasonable period of time commensurate with typical cycles of manufacture, storage, sales, and end-user use. If not, the formulation is unlikely to be commercially viable. The period during which these parameters remain within acceptable norms of use is typically referred to as the shelf life. Conventional inhaled formulations often have stability problems which are often thought to arise from changes in the particle-particle interactions in the formulation. Without wishing to be bound by a particular theory, the disclosed composite particles are believed to simplify the range and nature of particle-particle interactions, and thus it is to be expected that the disclosed compositions comprising the composite particles will have improved stability properties compared to conventional formulations with the same amount of active and excipient. Stability studies are typically carried out by placing samples of the material in environmental chambers with specified temperature and humidity conditions. At designated times, samples are removed and assayed for the given property or parameter of interest. For the disclosed composite particles, the samples would be assayed for ED, FPF, MMAD or any of the other parameters described herein. A typical study would involve analysis of samples 1, 3, 7, 14, 21, and 28 days; and, 2, 3, 4, 6, 9, 12, 18 and 24 months.

b. Composite Particle Characteristics

In one aspect, the invention relates to composite particles comprising millable grinding matrix and a pharmaceutically active agent with appropriate stability properties. In a further aspect, the stability of the composite particles comprising millable grinding matrix and a pharmaceutically active agent is measured after storage at conditions selected 25° C., 30° C., 35° C., 40° C., 25° C./60% relative humidity, 30° C./65% relative humidity and 40° C./75% relative humidity. In a still further aspect, the stability of the composite particles comprising millable grinding matrix and a pharmaceutically active agent is measured after storage for a period of time selected from 1 month, 3 months, 6 months, 9 months, 12 months, 18 months and 2 years. In a yet further aspect, the stability of the composite particles comprising millable grinding matrix and a pharmaceutically active agent is measured by determining the value of a specific property at the beginning of storage and the percentage change from the property at the beginning of storage at a later time less than or equal to a percentage selected from 0.1%, 0.2%, 0.3%, 0.4%, 0.5%, 0.75%, 1.0%, 1.5%, 2.0%, 3.0%, 4.0%, 5.0%, 6.0%, 7.0%, 8.0%, 9.0%, 10.0%, 12.5%, 15%, 17.5% and 20%. In an even further aspect, the specific property determined for stability is selected from ED, MMAD, FPF, and particle size.

6. Aerodynamic Properties (ED, FPF, GSD, and MMAD)

a. Methods for Determining

Delivery of a dose of powder from a dry powder inhalation device is less than perfect. A number of parameters are used to described the amount of powder in the device is delivered (or anticipated to be delivered) to the lungs. The FPF is defined as the fraction of pharmaceutically active agent that has an aerodynamic diameter less than about 4 to about 6 µm. The MMAD is defined as the aerodynamic diameter at which 50% of the particles by mass are larger and 50% are smaller. Another parameter useful in discussing these particular properties is the geometric standard deviation (GSD), which is a measure of the spread of an aerodynamic particle size distribution. It is typically calculated using the formula: $GSD=(d84/d16)^{1/2}$. For the parameters ED, FPF, GSD and MMAD, the values are dependent upon the device used to carryout the measurements. For example, ED, FPF, GSD, and MMAD can be determined using a MSLI with induction port, an CI with induction port and preseparator, or a NGI with induction port and preseparator.

In one aspect, the invention relates to composite particles wherein the parameters of ED, FPF, GSD and MMAD are determined using a NGI with induction port and preseparator. In a still further aspect, the composite particle parameters of ED, FPF, GSD and MMAD are determined using a device selected from a MSLI with induction port, an CI with induction port and preseparator, or a NGI with induction port and preseparator. It should be noted, for the disclosed composite particles, the pharmaceutically active agent is uniformly aggregated into the composite particles, thus the ED, FPF, GSD and MMAD for the pharmaceutically active agent is also an indicator of these properties for the composite particles.

ED provides an indication of the delivery of a drug formulation from a suitable inhaler device after a firing or dispersion event. More specifically, for dry powder formulations, the ED is a measure of the percentage of powder which is drawn out of a unit dose package and which exits the mouthpiece of an inhaler device. The ED is defined as the fraction of the total dose available in the device delivered by an inhaler device. The ED is experimentally determined by placing a dose of dry powder, typically in unit dose form, into a suitable dry powder inhaler which is then actuated, dispersing the powder. The total amount of powder found to have left the device is then measured and compared to the nominal dose. This measurement can be done when impactor/impinger testing is performed on the powder. The consistency of the ED is important, thus several doses should be measured and the consistency between the doses calculated. One way to measure this is as a RSD from the average emitted dose, which is typically given as a percent RSD (% RSD).

The FPF is one of the most important predictors of in vivo performance for a dry powder formulation and device combination. As described above, FPF is the fraction relative to the emitted dose unless otherwise specified, wherein the ED is defined as the fraction of the total dose available in the device delivered by an inhaler device, and it is often expressed as a percentage of the total dose. In some cases, the FPF relative to the total recovered dose (TRD) is specified and is indicated as "FPF(TRD)." The total recovered dose is the sum of emitted dose and the dose remaining in the device and/or dose packaging. Additional parameters of interest which are specific to composite particles comprising two or more pharmaceutically active agents are the MMAD uniformity ratio and FPF uniformity ratio. Both of these are defined and discussed above.

b. Composite Particle Characteristics

In one aspect, the invention relates to composite particles comprising millable grinding matrix and a pharmaceutically active agent with appropriate aerodynamic properties. In a still further aspect, the composite particles are capable of providing an aerosol with a FPF of emitted dose of the pharmaceutically active agent of greater than or equal to about 10% when delivered from a dry powder inhaler and analyzed with a NGI with an induction port and a preseparator. In a yet further aspect, the composite particles are capable of providing an aerosol with a related standard deviation (RSD) of the FPF of emitted dose of the pharmaceutically active agent of less than or equal to about 10% when delivered from a dry powder inhaler and analyzed with a NGI with an induction port and a preseparator. In an even further aspect, the composite particles are capable of providing an aerosol with a FPF of total recovered dose of the pharmaceutically active agent of greater than or equal to about 30% when delivered from a dry powder inhaler and analyzed with a NGI with an induction port and a preseparator.

In a further aspect, the composite particles are capable of providing an aerosol with a mass median aerodynamic diameter (MMAD) of the composite particles from about 1 μm to about 10 μm when delivered from a dry powder inhaler and analyzed with a NGI with an induction port and a preseparator. In a yet further aspect, the mass median aerodynamic diameter (MMAD) is from about 1 μm to about 7 μm. In a still further aspect, the MMAD is from about 1.5 μm to about 5 μm. In an even further aspect, the MMAD is from about 2 μm to about 5 μm. In a still further aspect, the MMAD is from about 2 μm to about 4 μm.

In a further aspect, the composite particles when delivered from a dry powder inhaler and analyzed with a NGI are capable of providing an aerosol with a mass median aerodynamic diameter (MMAD) of the composite particles from about 1 μm to about 10 μm and a FPF of the pharmaceutically active agent of at least about 10%. In a still further aspect, the composite particles are capable of providing an aerosol with an ED of greater than or equal to about 70% when delivered from a dry powder inhaler and analyzed with a NGI with an induction port and a preseparator. In a yet further aspect, the composite particles are capable of providing an aerosol with an emitted dose with a RSD of less than or equal to about 10% when determined on at least three samples delivered from a dry powder inhaler and analyzed with a NGI with an induction port and a preseparator.

In a further aspect, the composite particles comprising millable grinding matrix and a pharmaceutically active agent have the ED, FPF, GSD MMAD measured using a MSLI with induction port, an CI with induction port and preseparator, or a NGI with induction port and preseparator. In a yet further aspect, the composite particles comprising millable grinding matrix and a pharmaceutically active agent have the ED, FPF, GSD MMAD measured using a NGI with a USP induction port and preseparator.

In a further aspect, the composite particles comprising a millable grinding matrix and a pharmaceutically active agent have an ED greater than or equal to a percentage selected from 70%, 75%, 80%, 85%, 87.5%, 90%, 92.5%, 95%, 96%, 97%, 98% and 99%. In a yet further aspect, the composite particles comprising millable grinding matrix and a pharmaceutically active agent have a % RSD of three or more measurements of the ED less than or equal to a percentage selected from 0.1%, 0.2%, 0.3%, 0.4%, 0.5%, 0.75%, 1.0%, 1.5%, 2.0%, 3.0%, 4.0%, 5.0%, 6.0%, 7.0%, 8.0%, 9.0% and 10.0%. In a still further aspect, the ED determined for the pharmaceutically active agent is same or about the same ED for the composite particles. In an even further aspect, the pharmaceutically active agent is uniformly aggregated in the disclosed composite particles, thus the ED determined for the pharmaceutically active agent also an indicator of the ED for composite particles.

In a further aspect, the composite particles comprising a millable grinding matrix and a pharmaceutically active agent have an FPF with an MMAD less than or equal to a size selected from the group consisting of: 4.0 μm, 4.1 μm, 4.2 μm, 4.3 μm, 4.4 μm, 4.5 μm, 4.6 μm, 4.7 μm, 4.8 μm, 4.9 μm, 5.0 μm, 5.1 μm, 5.2 μm, 5.3 μm, 5.4 μm, 5.5 μm, 5.6 μm, 5.7 μm, 5.8 μm, 5.9 μm and 6.0 μm. In a yet further aspect, the composite particles comprising millable grinding matrix and a pharmaceutically active agent have an FPF greater than or equal to a percentage selected from 10%, 20%, 30%, 35%, 40%, 45%, 50%, 55%, 60%, 65%, 70%, 75%, 80%, 85% and 90%. In a still further aspect, the composite particles comprising a millable grinding matrix and a pharmaceutically active agent have an FPF (TRD) greater than or equal to a percentage selected from 10%, 20%, 30%, 35%, 40%, 45%, 50%, 55%, 60%, 65%, 70%, 75%, 80%, 85% and 90%. In an even further aspect, the composite particles comprising millable grinding matrix and a pharmaceutically active agent have a % RSD of three or more measurements of the FPF or FPF (TRD) less than or equal to a percentage selected from 0.1%, 0.2%, 0.3%, 0.4%, 0.5%, 0.75%, 1.0%, 1.5%, 2.0%, 3.0%, 4.0%, 5.0%, 6.0%, 7.0%, 8.0%, 9.0% and 10.0%. In one aspect the FPF is about 50%-60% and the MMAD is 2 μm to 4 μm (e.g., 2.2 μm to 3.8 μm, 2.4 μm to 3.6 μm, 2.4 μm to 3.4 μm, 2.5 μm to 3.1 μm or 2.6 μm to 3.0 μm. In a still further aspect, the FPF or FPF (TRD) determined for the pharmaceutically active agent is same or about the same FPF or FPF (TRD) for the composite particles. In an even further aspect, the pharmaceutically active agent is uniformly aggregated in the disclosed composite particles, thus the FPF or FPF (TRD) determined for the pharmaceutically active agent also an indicator of the FPF or FPF (TRD) for composite particles.

In a further aspect, the composite particles comprising a millable grinding matrix and a pharmaceutically active agent have an MMAD less than or equal to a size selected from about 10,000 nm, 8000 nm, 6000 nm, 5000 nm, 4500 nm, 4000 nm, 3500 nm, 3250 nm, 3000 nm, 2900 nm, 2800 nm, 2700 nm, 2600 nm, 2500 nm, 2400 nm, 2300 nm, 2200 nm, 2100 nm, 2000 nm, 1900 nm, 1800 nm, 1700 nm, 1600 nm and 1500 nm. In a still further aspect, the composite particles comprising a millable grinding matrix and a pharmaceutically active agent have an MMAD greater than about 1,000 nm.

In a further aspect, the composite particles comprising a millable grinding matrix and a pharmaceutically active agent have a GSD equal or less than the ratio selected from the group consisting of: 4, 3.5, 3, 2.9, 2.8, 2.7, 2.6, 2.5, 2.4, 2.3, 2.2, 2.1, 2.0, 1.9, 1.8 and 1.7.

In a further aspect, the composite particles have a fine particle fraction ratio of the first pharmaceutically active agent and second pharmaceutically active agent less than or equal to about 1.2 when delivered from a dry powder inhaler and analyzed with a NGI with an induction port and a preseparator.

In a further aspect, the composite particles have a MMAD uniformity ratio of less than or equal to about 1.2 when delivered from a dry powder inhaler and analyzed with a NGI with an induction port and a preseparator, wherein the distribution of each of the first and second pharmaceutically active agent is assayed and each is used to calculate an MMAD for the composite particle.

In a further aspect, the composite particles comprising a millable grinding matrix and at least two pharmaceutically active agents have a FPF uniformity ratio less than or equal to ratio selected from about 1.002, 1.005, 1.0075, 1.01, 1.0125, 1.015, 1.0175, 1.02, 1.03, 1.04, 1.05, 1.075, 1.02, 1.05, 1.075, 1.1, 1.125, 1.15 and 1.2. Ina yet further aspect, the composite particles comprising a millable grinding matrix and at least two pharmaceutically active agents have a MMAD uniformity ratio less than or equal to a ratio selected from about 1.002, 1.005, 1.0075, 1.01, 1.0125, 1.015, 1.0175, 1.02, 1.03, 1.04, 1.05, 1.075, 1.02, 1.05, 1.075, 1.1, 1.125, 1.15 and 1.2.

E. Inhalable Composition

In one aspect, the invention relates to an inhalable composition of pharmaceutically-active composite particles produced by a method comprising the steps of: (a) providing composite particles of a millable grinding matrix and a solid pharmaceutically-active agent, wherein the pharmaceutically-active agent within the composite particles has an average particle size of from about 50 nm to about 3 µm; and, (b) milling in a mill without milling bodies the composite particles for a time period sufficient to produce composite particles of the grinding matrix and the solid pharmaceutically-active agent for a time period sufficient to produce composite particles of the grinding matrix and the pharmaceutically-active agent with an effective aerodynamic particle size of from about 1 µm to about 20 µm.

In a further aspect, the invention relates to an inhalable pharmaceutically-active composition comprising: a plurality of composite particles of a millable grinding matrix and a solid pharmaceutically-active agent, wherein the composite particles of the grinding matrix and the pharmaceutically-active agent have an effective aerodynamic particle size of from about 1 μm to about 20 μm; and, wherein the pharmaceutically-active agent within the composite particles has an average particle size of from about 50 nm to about 3 μm.

F. Medicaments

1. Manufacture of Medicaments

In one aspect, the invention relates the manufacture of a medicament comprising the disclosed composite particles comprising a pharmaceutically active agent and a millable grinding matrix. In a further aspect, the medicament can further comprise one or more of each of a pharmaceutically acceptable carrier, milling aid, facilitating agent, pharmaceutically acceptable excipients, or other agents commonly used in the preparation of pharmaceutically acceptable inhaled compositions.

In a further aspect, the medicament can be formulated into a suitable device for administration by oral inhalation. Actual dosage levels of the pharmaceutically active agent in the medicament of the invention may be varied in accordance with the nature of the pharmaceutically active agent material. In a yet further aspect, the dosage level is varied due to differences in the therapeutically effective amount when medicament comprises the disclosed composite particles. Ina still further aspect, the medicament comprising the disclosed composite particles has an improved efficacy and a lower dose is required for a therapeutically effective amount.

In a further aspect, a disclosed composite particle can be combined into a medicament with another pharmaceutically active agent material, or even the same pharmaceutically active agent material. In a still further aspect, the medicament can have different release characteristics—early release from the pharmaceutically active agent material, and later release from a larger average size pharmaceutically active agent material.

a. Facilitating Agent

In a further aspect, the facilitating agent is selected from one or more of lecithin; soy lecithin, dipalmitoyl phosphatidylcholine, phosphatidylglycerol, dipalmitoyl phosphatidyl ethanolamine, dipalmitoyl phosphatidylinositol, phospatidylcholine, phosphatidylethanolamine, phosphatidylglycerol, phosphatidylinositol, phosphatidylserine, phospholipid, sodium stearyl fumarate, sodium stearyl lactylate, zinc stearate, magnesium stearate, calcium stearate, sodium stearate, and lithium stearate.

In a further aspect, the facilitating agent is selected from a solid state fatty acids. In yet further aspect, the solid state fatty acid is selected from palmitic acid, stearic acid, erucic acid, and behenic acid, or derivatives thereof such as esters and salts. In a still further aspect, the facilitating agent is selected from lauric acid and a lauric acid salt. In an even further aspect, the lauric acid salt is selected from sodium lauryl sulphate and magnesium lauryl sulphate. In a still further aspect, the facilitating agent is a triglyceride. In a yet further aspect, the triglyceride is selected from Dynsan 118 and Cutina HR.

In a further aspect, the facilitating agent is an amino acid. In yet further aspect, the amino acid is selected from aspartic acid, glutamic acid, leucine, isoleucine, lysine, valine, methionine, phenylalanine, glycine, arginine, aspartic acid, glutamic acid, cysteine, alanine, serine, N-acetyl-cysteine, phenylalanine, lysine, or pharmaceutically acceptable derivatives, salts, solvates, hydrates, and polymorphs thereof.

In a further aspect, the facilitating agent is selected from peptides and polypeptides having molecular weight from 0.25 to 1000 KDa. In a yet further aspect, the facilitating agent is selected from gelatine, hypromellose, PEG 6000, PEG 3000 or other PEGS, Tween 80, and Poloxamer 188.

b. Carrier Excipient

In a further aspect, the carrier excipient is selected from mannitol, sorbitol, Isomalt, xylitol, maltitol, lactitol, erythritol, arabitol, ribitol, glucose, fructose, mannose, galactose, anhydrous lactose, lactose monohydrate, sucrose, raffinose, ribitol, maltose, sorbose, cellobiose, sorbose, trehalose, inulin, and Isomalt. In a yet further aspect, the carrier excipient is a sugar or a polyol. In a still further aspect, the carrier excipient is lactose or mannitol. In an even further aspect, the carrier excipient is lactose monohydrate.

In a further aspect, the diameter of the carrier excipient particles is between about 50 μm and about 1000 μm. In a still further aspect, the diameter of the carrier excipient particles is between about 60 μm and about 250 μm. In a yet further aspect, the diameter of the carrier excipient particles is between about 90 μm and 250 μm.

2. Uses of Medicaments

Therapeutic uses of the disclosed composite particles, inhalable composites, and medicaments comprising the disclosed composite particles include pain relief, anti-inflammatory, anti-infective, migraine, asthma, COPD and other disorders that require the pharmaceutically active agent to be administered with a high bioavailability. In a further aspect, the pharmaceutically active agent has optimal effect when delivered locally to the lung. Alternatively, there are therapeutic uses wherein optimal clinical benefit is achieved with rapid bioavailability of a pharmaceutically active agent, e.g., relief of pain. In a still further aspect, the medicament comprising the disclosed composite particles is used to treat a pain disorder. In a yet further aspect, the pain disorder is selected from neuropathic, nociceptive, acute, chronic, and disease-specific path (e.g., pain associated with osteoarthritis or fibromyalgia). In a further aspect, analgesics, such as cyclooxygenase inhibitors, e.g., aspirin or NSAIDs, may be prepared as medicaments according to the present invention.

In a further aspect, medicaments comprising the disclosed composite particles can also be used for treatment of eye disorders. That is, the pharmaceutically active agent can be formulated for administration on the eye as an aqueous suspension in physiological saline, or a gel. In a still further aspect, the pharmaceutically active agent can be prepared in a powder form for administration via the nose for rapid central nervous system penetration.

In a further aspect, medicaments comprising the disclosed composite particles can be used for the treatment of cardiovascular disease. In a yet further aspect, the cardiovascular disease treated is angina pectoris. In a still further aspect, the pharmaceutically active agent is molsidomine. The clinical benefit and side effect profile of molsidomine can be improved by delivery to the lungs. Without wishing to be bound by a particular theory, such improvement can be attributed to enhanced bioavailability.

In a further aspect, medicaments comprising the disclosed composite particles can be used to treat treatment of hair loss, sexual dysfunction, or dermal treatment of psoriasis.

G. Method of Treating a Patient

1. Treating a Patient

In one aspect, the invention relates to a method of treating a patient having a need for treatment of a disorder, the method comprising the step of administering by inhalation an effective amount of an inhalable pharmaceutically-active composition comprising: a plurality of composite particles of a millable grinding matrix and a solid pharmaceutically-active agent, wherein the composite particles have an effective aerodynamic particle size of from about 1 µm to about 20 µm; and, wherein the pharmaceutically-active agent within the composite particles has an average particle size of from about 50 nm to about 3 µm.

In a further aspect, the treatment is preventing. In a still further aspect, the patient has been diagnosed with the disorder prior to administration.

In a further aspect, the disorder that is treated is selected from chronic obstructive pulmonary disease, acute asthma, chronic asthma, severe asthma, allergic asthma, acute respiratory distress syndrome, infant respiratory distress syndrome, reversible airways disease, and cystic fibrosis.

In a further aspect, the disorder that is treated is an infection. In a yet further aspect, the infection is selected from bacterial, fungal, and viral. In a still further aspect, the infection is a bacterial infection. In an even further aspect, the infection is a viral infection. In a still further aspect, the infection is a fungal infection.

In a further aspect, the disorder that is treated is a pain disorder. In a yet further aspect, the pain disorder is selected from neuropathic, nociceptive, acute, chronic, and disease-specific path (e.g., pain associated with osteoarthritis or fibromyalgia).

In a further aspect, the disorder that is treated is selected from cystic fibrosis, tuberculosis, pneumonia, severe acute respiratory syndrome, infection, pulmonary embolus, tuberculosis, pulmonary arterial hypertension, pulmonary edema, and pneumocystis pneumonia. In a still further aspect, the disorder that is treated is selected from eye disorders, hair loss, sexual dysfunction, and cardiovascular disease. In a yet further aspect, the cardiovascular disease is angina pectoris.

2. Inhaled Delivery

Dry powder formulations of active pharmaceutical ingredients (including blends of active and excipients) for oral inhalation are important tools for the delivery of medications. Common uses have been in the delivery of pharmaceutical agents that act locally, e.g., asthma medications delivered to the lungs. This delivery route is also becoming more important for systemic delivery. Two of the critical parameters for inhaled dry powder formulations are particle size and the flowability of the powder. The powder in the device used by the patient needs to flow well so that a full and consistent dose of the powder formulation leaves the device. If the powder flow is poor, powder may remain behind in the device or stick to the device as it is dispensed. The particle size of the powder is then critical to ensure that the powder (and active material) is (are) delivered to the required absorption zone.

One common measure of particle size used to characterize dry powder formulations is the Mass Median Aerodynamic Diameter (MMAD). As described above, MMAD the aerodynamic diameter at which 50% of the particles by mass are larger and 50% are smaller. Methods of measuring aerodynamic particle size are described above, including the Anderson Cascade Impactor or the New Generation Impactor. Alternatively, particle size measures such as the median particle size measured by a laser diffraction dry powder analysis are also useful. However, MMAD is the preferred measurement for an inhaled formulation as it better approximates the aerodynamic properties of the lungs. In a further aspect, an inhaled formulation has an MMAD less than about 10 µm. In a still further aspect, an inhaled formulation has an MMAD less than about 5 µm. In a yet further aspect, an inhaled formulation has a median particle size is preferably less than about 10 µm, wherein the dry powder sizing is determined by laser diffraction.

3. Packaging and Devices

In order to deliver a powder to the lungs by oral inhalation the powder must be packaged into a suitable device. The device must be suitable to aerosolise the powder during the inhalation process. In a further aspect, the device allows for a dose, packaged into individual packing, to be inserted into the device prior to delivery. In a yet further aspect, the device has a reservoir for delivering multiple doses. In a still further aspect, a device that has two or more individual doses of powder packaged into individual packing and assembled or inserted into the device allowing a device to deliver multiple doses. Suitable devices can be reusable or disposable.

In a further aspect, the device is selected from the group consisting of: 3M Conix™ 1 DPI (3M), 3M Conix™ 2 DPI (3M), 3M™ Taper DPI (3M), Acu-Breathe (Respirics), Aspirair (Vectura), Cricket™ inhaler (Mannkind), Dreamboat™ (Mannkind), Duohaler (Vectura), Easyhaler® (Orion), Flowcaps® (Hovione), Genuair® (Almirall Sofotec), Gen-X® (Cambridge Consultants), GyroHaler (Vectura), Manta Multi Dose (Manta), Manta Single Dose (Manta), MicroDose DPI (MicroDose Therapeutx), Next™ (Chiesi Farmaceutici), Novolizer® (Meda/Almirall Sofotec), Prohaler™ (Valois), SkyeHaler™ (Skye Pharma), Smartinhaler (Nexus6), Solis™ (Oriel Therapeutics/Sandoz), Sun DPI (Sun pharmaceuticals/Cambridge Consultants), TAIFUN® (Akela Pharma/Focus Inhalation), Twin Caps™ (Hovione), Twincer™ (Groningen University), Xcaps (Hovione), Spinhaler (Aventis), Rotahaler (GlaxoSmithKline), Inhalator (Boehringer-Ingeheim), Cyclohaler (Pharmachemie), Handihaler (Boehringer-Ingeheim), Aerolizer (Novartis), FlowCaps (Hovione), TwinCaps (Hovione), Turbohaler (Astra Zeneca), Diskhaler (GlaxoSmithKline), Diskus/Accuhaler (GlaxoSmithKline), Aerohaler (Boehringer-Ingeheim), Easyhaler (Orion Pharma), Ultrahaler (Aventis), Pulvinal (Chiesi), Novolizer (ASTA), MAGhaler (Boehringer-Ingeheim), Taifun (LAB Pharma), Eclipse (Aventis), Clickhaler (Innoveta Biomed), Asmanex Twisthaler (Schering-Plough Corporation), Airmax (Norton Healthcare), CRC-749 (Pfizer), Omnihaler (Innoveta Biomeds Ltd), Actispire (Britania), DirectHaler (Direct-Haler), JAGO (SkyPharma), Airmax (Norton Healthcare), Turbospin (PH & T), AIR (Alkermes), Cyclovent (Pharmachemie), Dispohaler (AC Pharma). Microhaler (Harris Pharmaceutical), Technohaler (Innoveta Biomed Ltd), Spiros (Dura), Bulkhaler (Asta Medica), Miat-Haler (MiatSpA), Monodose Inhaler (MiatSpA), Acu-Breath (Respirics), Swinghaler® (Otsuka Pharmaceutical Co. Ltd), Pfeiffer (Pfeiffer GmbH), Certihaler (Novartis Pharma/Skye Pharma), Otsuka DPI/breath actuated (Otsuka Pharmaceutical Co. Ltd), Flexihaler (Astra Zeneca) and devices that are the same but have different names or are made by different companies, and devices that are similar or are generic copies of these devices.

In a further aspect, the device is assembled with or has inserted into it the packaging that carries the powder ready for dispensing by the device just prior to the inhalation process. For example, hard capsules are used as packaging. In a still further aspect, hard capsules used as packaging are made from gelatine or HMPC. In a yet further aspect, the capsules have a size that is selected from the group consisting of: size 4, size 3, size 2, size 1 and size 0. In an even further aspect, the capsules are further packaged into individual blister packs. In a still further aspect, the blister pack is formed from aluminium foil laminates at the top and bottom. In devices that contain multiple doses specialised packaging is used. For example, the packaging used can contain multiple doses is small blister packs formed from aluminium foil laminates at the top and bottom. In some instances, it is desirable that the blister packs are in the form of strips of individual blisters. In a further aspect, the foil blisters are formed in a disk or ring.

H. Experimental

1. Materials

The following materials were used in the examples: active pharmaceutical ingredients (salbutamol) were sourced from commercial suppliers, the lactose from DMV-Fonterra, and the lecithin (USP grade) from Spectrum chemicals. Ventolin Rotocaps (200 μg of salbutamol as salbutamol sulphate) were obtained as commercial supplies. Unless otherwise indicated, where materials in a composition are given as a percent it is in weight percent (% w/w), unless otherwise indicated.

2. General Methods a. Attritor-Type Mill

Dry-milling experiments were performed using a 1S Union Process attritor mill with a 1.5 gallon grinding chamber. The grinding media consisted of 20 kg of ⅜" stainless steel balls. A total of 1 kg of powder was milled for each batch. The mill was loaded through the loading port, with the grinding media added initially, then followed by the dry powders. The milling process was conducted with the jacket cooled to 13-16° C. and the shaft rotating at 400 rpm. Upon completion of milling, the milled powder was discharged from the mill through the bottom discharge port at 77 rpm.

b. Air Jet Milling:

Two air jet milling conditions were used.

Ten inch air jet milling was performed in a 10" Spiral Jet Mill (Powdersize Inc) at a feed rate of 10 kg/hour. Between 500-1000 grams of powder was fed through the mill for each sample.

Four inch air jet milling was performed in a 4" Spiral Jet Mill (Powdersize Inc) at variable feed rates and pressures. Between 50-400 grams of powder was fed through the mill for each sample.

c. Laser Diffraction

The particle size distribution (PSD) was determined using a Malvern Mastersizer 2000. For wet (aqueous) measurements of the active material a Malvern Hydro 2000S pump unit was used. For dry particle size measurements of the composites a Scirocco 2000 measurement unit was used.

For the wet measurements the following settings were used: Measurement Time: 12 seconds, Measurement cycles: 3. Final result generated by averaging the 3 measurements. Samples were measured by adding dry powder to saturated aqueous salbutamol containing ~0.03% PVP. Up to 2 minutes of sonication was applied within the measurement cell before measurement. The refractive index of the active was set to 1.56 with the absorption at 0.01.

For dry measurements a pressure of 3-3.5 bar was used for the measurements. The refractive index of lactose was used for analysis (1.35 with the absorption at 0.01.)

Other laser diffraction measurement of the composites were measured with isoparG as a solvent. These were performed on a Microtrac S3000 instrument using a 10 second run time. The refractive index of the composite was set at 1.51 and the solvent was 1.42.

d. Time of Flight Measurements:

Time of flight measurements were measured on a TSI Aerosizer with an Aerodisperser set to a medium shear force and feed rate. Deagglomeration was set to normal and pin vibration was on. The particle size statistics are a volume distribution.

e. Aerodynamic Particle Size Distribution:

Aerodynamic Particle Size Distribution was measured on Next Generation Pharmaceutical Impactor with stainless steel collection cups, preseparator and a USP induction port. Testing was performed with a total flow of 4 L with a pressure drop of 4 kPa up to a maximum of 100 L/min. The actual flow was approximately 98-100 L/min. The commercial Ventolin Rotocaps where used as received. Other powders (~20 mg) were filled into Size 3 HPMC inhalation capsules or machine filled (~24.5 mg) using a Harro Höfliger Omnidose Drumfiller (see section g for settings) into Size 3 HPMC inhalation capsules. All capsules were tested in a Monodose Inhaler. HPLC analysis was used to assay the active.

f. Powder Uniformity

Ten samples were taken from the bulk blend at locations throughout the sample. These were then assayed by HPLC and expressed as a % RSD over those 10 samples. For some batches an assay by HPLC was also measured.

g. Automatic Powder Dispensing

A Harro Höfliger Omnidose Drumfiller was used to dose powder to measure the accuracy and precision of powder dispensing. The dispenser was set to 35 cycles/min, a 500 mbar product vacuum, a 300 mbar dispense pressure with 2 stirrer rotations (180% speed) and 2 shots per cavity. The powder was filled into stainless steel thimbles for accurately weighing the mass of powder dispensed.

h. Scanning Electron Microscopy (SEM)

SEM's were measured on a Zeiss 1555 VPSEM. The powder samples were applied to a carbon tab on the SEM stub and coated with 3-5 nm of platinum before imaging.

3. Production of Composite Particles with 10% Salbutamol in Lactose Monohydrate a. Dry-Milling of 10% Salbutamol in Lactose Monohydrate:

Four batches (labeled as 1A, B, C, and D) of 10% salbutamol in lactose monohydrate with 1% (w/w) lecithin were dry-milled at 1 kg scale for 15 minutes. The particle size of the pharmaceutically active agent was measured and the data are shown in Table 1. The particle size data of the composite particle comprising salbutamol and lactose are also shown in Table 1.

TABLE 1

| | Active particle Size (Wet (aqueous) laser diffraction) | | | | Composite Size (Dry laser diffraction) | | |
|---|---|---|---|---|---|---|---|
| Batch No. | D[50] μm | % < 0.2 μm | % < 0.3 μm | % < 0.5 μm | % < 1.0 μm | D[50] μm | D[90] μm | D[4,3] μm |
| 1A | 0.137 | 72 | 85 | 89 | 90 | 8.3 | 31.8 | 13.1 |
| 1B | 0.137 | 80 | 95 | 96 | 96 | 8.2 | 30.0 | 12.4 |
| 1C | 0.136 | 79 | 92 | 93 | 93 | | | |
| 1D | 0.129 | 84 | 98 | 100 | 100 | 8.8 | 32.3 | 13.4 | b. Air Jet Milling

Material from batches 1A-D was air jet-milled in the ten inch setup at four different pressures, 7.24 Bar (batch 2A), 4.83 Bar (batch 2B), 3.45 Bar (batch 2C) and 1.72 Bar (batch 2D). The particle size of the composite particles are shown in Table 2, and particle size was measured, as indicated, either by dry laser or wet laser diffraction using Isopar™ G as a solvent. Particle size of the pharmaceutically active agent, salbutamol, was determined after air jet-milling for batches 2A-D using wet laser diffraction and is shown in Table 3. The particle size of the composite particle after air jet-milling was determined by time of flight measurement and the data are shown in Table 4.

TABLE 2

| | Jet Mill Pressure (Bar) | Composite Size Dry laser diffraction | | | Composite Size (Wet (isoparG) laser diffraction) | |
|---|---|---|---|---|---|---|
| Batch No. | | D[50] μm | D[90] μm | D[4,3] μm | D[50] μm | D[90] μm |
| 2A | 7.24 | 1.8 | 4.2 | 2.2 | 2.4 | 4.7 |
| 2B | 4.83 | 2.2 | 5.3 | 2.6 | 2.9 | 5.6 |
| 2C | 3.45 | 2.5 | 6.8 | 3.1 | 3.7 | 7.1 |
| 2D | 1.72 | 3.5 | 9.5 | 4.4 | 4.8 | 10.8 |

TABLE 3

| | | Active particle Size (Wet (aqueous) laser diffraction) | | | | |
|---|---|---|---|---|---|---|
| Batch No. | Jet Mill Pressure (Bar) | D[50] μm | % < 0.2 μm | % < 0.3 μm | % < 0.5 μm | % < 1.0 μm |
| 2A | 7.24 | 0.127 | 84 | 96 | 96 | 99 |
| 2B | 4.83 | 0.128 | 84 | 97 | 98 | 99 |
| 2C | 3.45 | 0.137 | 75 | 86 | 88 | 92 |
| 2D | 1.72 | 0.127 | 83 | 97 | 98 | 99 |

TABLE 4

| | Jet Mill | Composite Size - Time of Flight | | |
|---|---|---|---|---|
| Batch No. | Pressure (Bar) | Mean (μm) | D[90] μm | D[4, 3] μm |
| 2A | 7.24 | 3.7 | 7.6 | 4.3 |
| 2B | 4.83 | 6.0 | 12.6 | 7.2 |
| 2C | 3.45 | 5.4 | 10.5 | 6.1 |
| 2D | 1.72 | 7.7 | 12.8 | 8.4 |

4. Production of Composite Particles with 1% Salbutamol in Lactose Monohydrate a. Dry-Milling of 1% Salbutamol in Lactose Monohydrate:

Another batch (labeled as 3A) comprising was dry-milled at 1 kg scale for 20 minutes with lactose monohydrate as the millable grinding matrix and comprising 1% salbutamol and 1% lecithin. The particle size data of the composite particle comprising salbutamol and lactose for Batch 3A are shown in Table 5.

TABLE 5

| | Composite Size - Dry laser diffraction | | |
|---|---|---|---|
| Batch No. | D[50] μm | D[90] μm | D[4, 3] μm |
| 3A | 7.9 | 48.9 | 17.0 | b. Air Jet Milling

Material from batch 3A was air jet-milled in the ten inch setup at 4.83 Bar (batch 3B). The particle size of the composite particles of batch 3B is shown in Table 6, and particle size was measured, as indicated, either by dry laser or wet laser diffraction using Isopar™ G as a solvent. Particle size of the pharmaceutically active agent, salbutamol, was determined after air jet-milling for batches 3B using wet laser diffraction. The particle size is shown in Table 7. The particle size of the composite particle after air jet-milling was determined by time of flight measurement and the data are shown in Table 8.

TABLE 6

| | Jet Mill Pressure (Bar) | Composite Size Dry laser diffraction | | | Composite Size (Wet (isoparG) laser diffraction) | |
|---|---|---|---|---|---|---|
| Batch No. | | D[50] μm | D[90] μm | D[4,3] μm | D[50] μm | D[90] μm |
| 3B | 4.83 | 2.4 | 6.1 | 3.0 | 3.5 | 7.0 |

TABLE 7

| | | Active particle Size (Wet (aqueous) laser diffraction) | | | | |
|---|---|---|---|---|---|---|
| Batch No. | Jet Mill Pressure (Bar) | D[50] μm | % < 0.2 μm | % < 0.3 μm | % < 0.5 μm | % < 1.0 μm |
| 3B | 4.83 | 0.132 | 87 | 100 | 100 | 100 |

TABLE 8

| | Jet Mill | Composite Size - Time of Flight | | |
|---|---|---|---|---|
| Batch No. | Pressure (Bar) | Mean (μm) | D[90] μm | D[4, 3] μm |
| 3B | 4.83 | 5.2 | 9.3 | 5.8 | c. Next Generation Impactor Measurements

Ventolin Rotacaps and powder from batch 3B were both evaluated through the NGI. Three capsules were analyzed for each sample (either Ventolin Rotocap or batch 3B, as indicated, wherein the pharmaceutically active agent in each was salbutamol). 6 months after the testing of batch 3B the bulk powder, which had been stored at ambient conditions, was split into two lots. One lot was used to handfill further capsules for NGI testing (3 capsules). The other lot was filled into capsules using an Omindose Drumfiller. These capsules (3 capsules tested) were tested 8 months after the initial NGI testing of batch 3B. In Table 9 and 10 the average of the three measurements and the relative standard deviation (RSD, %) between the three measurements are shown. The data shown in Table 9 and 10 show the mass of salbutamol in each of the various components and stages of the test apparatus determined by assay for salbutamol. The table indicates the size cutoff for each stage (assuming a flow of 100 L/min). The total recovered dose (TRD) is the sum of all material in the apparatus. The ED is the sum of material found in the induction port through to the MOF (filter), i.e. all the material except the residue in the capsule and device. The fine particle dose (FPD) is the amount of material calculated to be below an aerodynamic diameter of 5 µm. Calculations for FPD were carried out using the Copley Inhaler Testing Data Analysis Software (Copley Scientific Limited, Nottingham, UK).

The data from Table 9 and 10 was then used to evaluate the emitted dose as a percent of the TRD, the FPF, which is the percentage of particles below 5 µm, relative to either the ED and the TRD, as well as the MMAD. This data are shown in Table 11, which shows the emitted dose as a percent of the TRD, the FPF relative to the ED and the TRD as indicated, and the MMAD calculated from the NGI measurements.

TABLE 9

| Sample | Ventolin Rotacaps | | Batch 3B-Initial | |
|---|---|---|---|---|
| | Mass (µg) | % RSD | Mass (µg) | % RSD |
| Induction Port | 33.7 | 13.5 | 34.8 | 4.9 |
| Pre-separator | 86.0 | 4.7 | 5.7 | 6.3 |
| Stage 1 (6.1 µm) | 14.7 | 9.0 | 13.5 | 2.3 |
| Stage 2 (3.4 µm) | 18.2 | 12.5 | 24.4 | 3.0 |
| Stage 3 (2.2 µm) | 21.8 | 8.9 | 23.6 | 3.7 |
| Stage 4 (1.3 µm) | 23.3 | 10.3 | 23.1 | 4.3 |
| Stage 5 (0.7 µm) | 12.3 | 11.7 | 11.9 | 5.9 |
| Stage 6 (0.4 µm) | 3.0 | 24.0 | 3.7 | 9.4 |
| Stage 7 (0.2 µm) | 1.4 | 27.7 | 1.6 | 12.5 |
| MOF | 0.3 | 45.8 | 0.7 | 14.3 |
| Residual in Capsule & Device | 45.7 | 10.4 | 11.1 | 19.0 |
| Total recovered dose (TRD) | 260.5 | 1.7 | 154.1 | 0.2 |
| Emitted dose (ED) | 214.7 | 3.4 | 143.0 | 1.5 |
| Fine Particle Dose (FPD) (µg < 5 µm) | 74.6 | 6.7 | 81.9 | 4.3 |

TABLE 10

| Sample | Batch 3B-6 months | | Batch 3B-8 months | |
|---|---|---|---|---|
| | Mass (µg) | % RSD | Mass (µg) | % RSD |
| Induction Port | 26.8 | 45.3 | 34.3 | 0.2 |
| Pre-separator | 14.8 | 64.8 | 10.6 | 6.6 |
| Stage 1 (6.1 µm) | 14.6 | 6.5 | 17.8 | 9.3 |
| Stage 2 (3.4 µm) | 23.7 | 10.3 | 29.2 | 1.4 |
| Stage 3 (2.2 µm) | 20.0 | 5.7 | 24.9 | 5.6 |
| Stage 4 (1.3 µm) | 18.8 | 4.1 | 23.9 | 5.1 |
| Stage 5 (0.7 µm) | 8.8 | 2.4 | 11.9 | 1.9 |
| Stage 6 (0.4 µm) | 3.1 | 3.2 | 3.7 | 1.6 |
| Stage 7 (0.2 µm) | 0.9 | 12.4 | 1.2 | 24.7 |
| MOF | 0.3 | 33.3 | 0.5 | 24.7 |
| Residual in Capsule & Device | 17.2 | 52.2 | 11.7 | 7.8 |
| Total recovered dose (TRD) | 148.9 | 8.1 | 169.5 | 3.0 |
| Emitted dose (ED) | 131.7 | 2.5 | 157.8 | 2.7 |
| Fine Particle Dose (FPD) (µg < 5 µm) | 68.1 | 5.6 | 86.3 | 3.2 |

TABLE 11

| Sample | Ventolin Rotacaps | Batch 3B-Initial | Batch 3B 6 months | Batch 3B 8 months |
|---|---|---|---|---|
| % Emitted Dose | 82.4 | 92.8 | 88.7 | 93.1 |
| FPF (relative to the ED, %) | 34.7 | 57.3 | 51.8 | 54.7 |
| FPF (relative to the TRD, %) | 28.6 | 53.1 | 46.0 | 50.9 |
| MMAD (µm) | 2.6 | 2.6 | 3.0 | 2.9 |
| GSD | 2.3 | 2.1 | 2.2 | 2.2 |

The data in this example shows that the formulation for oral inhalation produced by this invention is superior to a conventional produced formulation (Ventolin Rotacaps). The MMAD for both samples was shown to be the same so a head to head comparison is truly valid. The first key superiority is the emitted dose which is 10% higher for batch 3B as little powder remains in the device after actuation. The key superiority is the FPF where batch 3B has also double the amount of active in the particle size range suitable for inhalation. The data also shows that the delivery of the dose is more consistent and uniform for batch 3B. For the ventolin sample the percent RSD for each of the stages is at least double those measured for batch 3B. This shows that batch 3B has a much more consistent particle size distribution from dose to dose compared to the ventolin sample. This is important to the patient as the exact size of the particles will determine which part of the lung the active is delivered to. As the bioavailability and efficacy of the active is dependant on which part of the lung the particle settles variability in where the active settles will lead to variability in therapeutic effect.

The data for batch 3B measured after 6 and 8 months also shows little change from the initial testing which demonstrates that the invention described herein is capable of producing formulations with stable performance over time. The data of batch 3B at 8 months was also filled into the capsules using an automated filling machine. So the fact that there is little change in the aerodynamic properties also demonstrates that the powders produced by this invention can be successfully filled using automated equipment without determential changes to the powder properties.

d. Powder Uniformity

The powder uniformity of batch 3B was measured and the data is shown in Table 12. The data shows that the blend has excellent uniformity, even at this low active loading. It should also be noted that batch 3A was manufactured in Australia and transported to the USA for jet milling to become batch 3B and then the sample was transported to another facility for the uniformity tests. The fact that the content uniformity has been retained to such a high level is strong testament to the excellent uniformity properties of this material.

TABLE 12

| | Sample No. | | | | | | | | | | | RSD |
|---|---|---|---|---|---|---|---|---|---|---|---|---|
| | 1 | 2 | 3 | 4 | 5 | 6 | 7 | 8 | 9 | 10 | Ave | (%) |
| Batch 3B | 0.84 | 0.82 | 0.83 | 0.82 | 0.82 | 0.82 | 0.83 | 0.82 | 0.82 | 0.82 | 0.82 | 0.71 | e. Powder Flowability

A sample of batch 3B that was 6 months old was dispensed from a Harro Höfliger Omnidose Drumfiller. A set of 60 24.5 mg shots of powder were dispensed. The mean weight for this set was 24.53 mg. The minimum fill weight was 23.58 mg. The maximum fill weight was 25.37 mg. The relative standard deviation (% RSD) was 1.70.

5. Production of Composite Particles with Ipratropium Bromide and Salbutamol Sulfate in Lactose Monohydrate a. Dry-Milling of Ipratropium Bromide and Salbutamol Sulfate in Lactose Monohydrate:

Four batches (labeled as 4A, B, C, and D) of various %'s of ipratropium bromide and salbutamol sulfate in lactose monohydrate with 1% w/w lecithin were dry-milled at 1 kg scale for 20 minutes. The % of the two actives in each batch is shown in Table 13. The particle size data of the composite particles comprising ipratropium bromide, salbutamol sulfate and lactose are also shown in Table 13.

TABLE 13

| Batch No. | Ipratropium Bromide (% (w/w)) | Salbutamol Sulfate (% (w/w)) | Composite Size (Dry laser diffraction) | | |
|---|---|---|---|---|---|
| | | | D[50] µm | D[90] µm | D[4, 3] µm |
| 4A | 0.105 | | 8.2 | 36.1 | 14.4 |
| 4B | 0.42 | | 7.5 | 23.6 | 10.3 |
| 4C | 0.105 | 0.6 | 7.4 | 37.9 | 13.3 |
| 4D | 0.42 | 2.4 | 6.2 | 21.5 | 9.4 | b. Air Jet Milling

Material from each of batches 4A-D was divided into two and air jet-milled in the four inch setup at two different conditions. The lower energy condition was a pressure of 3.45 Bar and a relative feed rate of 385-425 Bar, the higher energy condition was a pressure of 4.14-4.48 Bar and a relative feed rate of 220-275 Bar. A relative feed rate of 220 is a target feed rate of 350 grams/hour. The details of how each batch was milled are shown in Table 14. The particle size of the composite particles are shown in Table 15, and particle size was measured, as indicated, either by dry laser or wet laser diffraction using Isopar™ G as a solvent.

TABLE 14

| Batch No. | Input Batch No. | Ipratropium Bromide (% (w/w)) | Salbutamol Sulfate (% (w/w)) | Jetmilling Pressure (Bar) | Feedrate (relative) |
|---|---|---|---|---|---|
| 4E | 4A | 0.105 | | 3.45 | 435 |
| 4F | 4A | 0.105 | | 4.14 | 275 |
| 4G | 4B | 0.42 | | 3.45 | 385 |
| 4H | 4B | 0.42 | | 4.48 | 220 |
| 4I | 4C | 0.105 | 0.6 | 3.45 | 425 |
| 4J | 4C | 0.105 | 0.6 | 4.14 | 255 |
| 4K | 4D | 0.42 | 2.4 | 3.45 | 385 |
| 4L | 4D | 0.42 | 2.4 | 4.14 | 250 |

TABLE 15

| Batch No. | Jet Mill Energy | Composite Size Dry laser diffraction | | | Composite Size (Wet laser diffraction) | |
|---|---|---|---|---|---|---|
| | | D[50] µm | D[90] µm | D[4,3] µm | D[50] µm | D[90] µm |
| 4E | low | 2.9 | 7.4 | 3.5 | 3.8 | 8.1 |
| 4F | high | 2.3 | 5.8 | 2.8 | 3.2 | 5.5 |
| 4G | low | 2.4 | 6.9 | 3.1 | 3.8 | 7.8 |
| 4H | high | 1.8 | 4.5 | 2.2 | 2.4 | 4.0 |
| 4I | low | 2.6 | 7.1 | 3.3 | 3.9 | 7.9 |
| 4J | high | 1.9 | 4.6 | 2.3 | 2.4 | 4.0 |
| 4K | low | 2.3 | 6.1 | 2.9 | 3.6 | 6.7 |
| 4L | high | 2.0 | 5.3 | 2.5 | 3.0 | 5.0 | c. Powder Uniformity

The assay of actives and the powder uniformity of batches 4E-L was measured by HPLC and the data is shown in Table 16. The data show that the powders have the correct assays and excellent uniformity, even at these very low active loading. It should also be noted that these batches were dry milled in Australia and transported to the USA for jet milling and then transported back to Australia for assay and uniformity tests. The fact that the content uniformity has been retained to such a high level despite this extensive transport is strong testament to the excellent uniformity properties of this material.

TABLE 16

| Batch No. | Jet Mill Energy | Assay by HPLC (% w/w) | | Content Uniformity (% RSD) | |
|---|---|---|---|---|---|
| | | IB | SS | IB | SS |
| 4E | low | 0.11 | | 4.5 | |
| 4F | high | 0.11 | | 0.8 | |
| 4G | low | 0.44 | | 2.4 | |
| 4H | high | 0.44 | | 1.5 | |
| 4I | low | 0.11 | 0.62 | 3.1 | 2.8 |
| 4J | high | 0.11 | 0.62 | 0.9 | 0.7 |
| 4K | low | 0.44 | 2.35 | 3.2 | 3.3 |
| 4L | high | 0.42 | 2.30 | 3.9 | 4.1 | d. Scanning Electron Microscopy (SEM)

Figure 2:
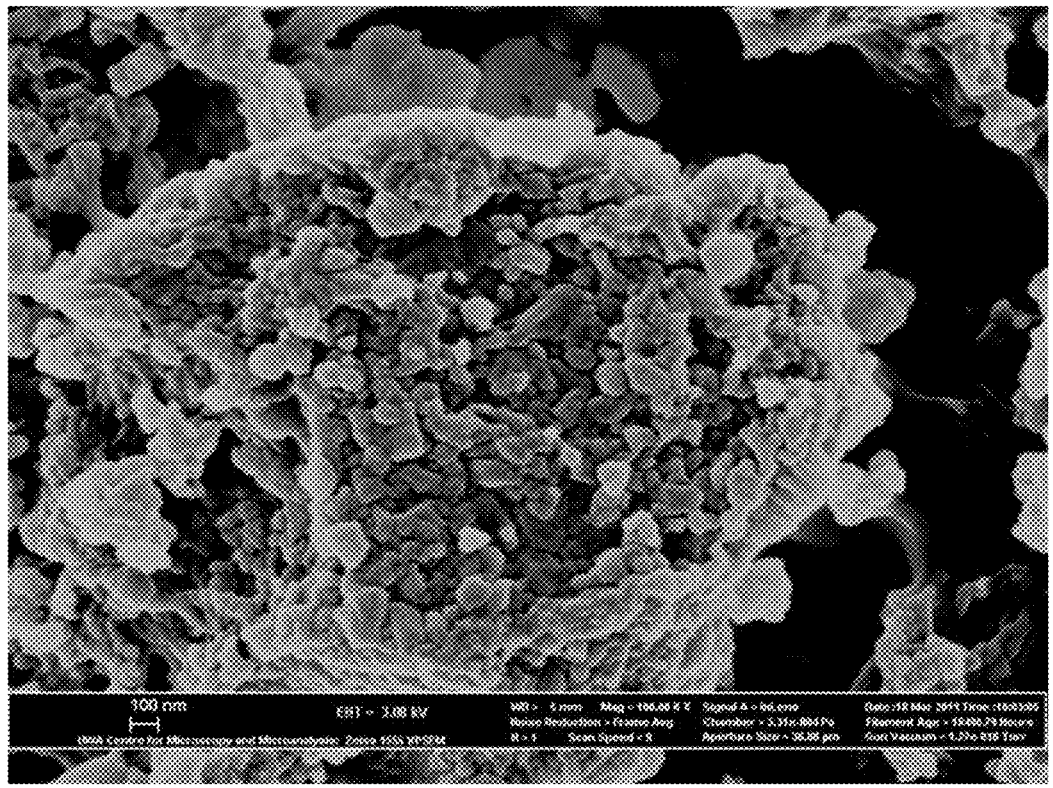

SEM images of one sample (4J) where taken and are shown in FIGS. 1-2. FIG. 1 is shown at a magnification of 10,000× and shows an overview of the composite size and shape. The image clearly shows the particles have an irregular shape and a primary particle size between 1-5 micron. FIG. 2 shows an images at high magnification show that the composite particles are an aggregate of matrix and active particles of order 200 nm or less. The figure also shows that the composite particles have high surface roughness on a nanometer scale.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I. Other Embodiments

In a further aspect, the pharmaceutically active agent is selected from one or more of alpha 1 antitrypsin, beclomethasone, budesonide, calcitonin, ciclesonide, ciprofloxacin, clarithromycin, clinafloxacin, cloxacillin, colistimethate, colistin, cromolyn, darotropium, desmopressin, dihydroergotamine, dirithromycin, elcatonin, enokizumab, epinastine, erdosteine, ergotamine, erythromycin, erythropoietin (EPO), etamiphylline, factor IX, fenspiride, fentanyl, floxacillin, flunisolide, flurisolide, flurithromycin, fluticasone, formoterol, glycopyrrolate, guaifenesin, hydrocortisone, indacaterol, insulin, insulin tropin, insulin-like growth factor (IGF), interferon alpha, interferon beta, interferon gamma, ipratropium, ipratropium, lebrikizumab, levocetirizine, levofloxacin, lomefloxacin, losmapimod, low molecular weight heparin (LMWH), mabuterol, masilukast, mecysteine, metaproterenol, methicillin, milveterol, mometasone, montelukast, muscarinic acetylcholine receptor antagonist and beta 2 adrenoceptor dual agonist (MABA), olodaterol, omalizumab, oxitropium, oxtriphylline, pirbuterol, Polymyxin B, pranlukast, procaterol, proinsulin, pyruvate, rifampicin, salbutamol, salmeterol, seratrodast, theophylline, tobramycin, tofimilast, tulobuterol, vancomycin, vasopressin, vilanterol, X-ray contrast agents, xylometazoline, zafirlukas, zileuton, or a pharmaceutically acceptable salt, solvate, hydrate, or polymorph thereof.

In a further aspect, the pharmaceutically active agent is an insulin. In a yet further aspect, the insulin is selected from a recombinant insulin, insulin purified from a mammal, substituted insulin, pro-insulin, semi-synthetic insulin, synthetic insulin, or a pharmaceutically acceptable salt, solvate, hydrate, or polymorph thereof. In an even further aspect, the insulin is selected from human recombinant insulin, insulin regular, insulin aspart, insulin aspart protamine, insulin detemir, insulin glargine, insulin glulisine, insulin isophane, insulin lispro, or a pharmaceutically acceptable salt, solvate, hydrate, or polymorph thereof.

In a further aspect, the pharmaceutically active agent is selected from beclomethasone, budesonide, ciclesonide, ciprofloxacin, colistin, dihydroergotamine, formoterol, fluticasone, insulin, ipratropium, mometasone, Polymyxin B, rifampicin, salbutamol, salmeterol, tobramycin, or a pharmaceutically acceptable salt, solvate, hydrate, or polymorph thereof.

In a further aspect, the pharmaceutically active agent is selected from AZD1419, AZD1981, AZD3199, AZD5069, AZD5423, AZD8683, AZD9164, AZD9668, GSK1325756, GSK159802, GSK2190915, GSK2245840, GSK256066, GSK573719, GSK610677, GSK681323, GSK961081, GW870086, PF184, PF3526299, PF3635659, PF3893787, PF4191834, PF4764793, PF610355, TD4208, and TD5959.

In a further aspect, the composite particle further comprises a second pharmaceutically active agent, the method producing composite particles of the matrix having the solid pharmaceutically active agent and the second pharmaceutically active agent dispersed therein. In a yet further aspect, the first and second pharmaceutically active agents are selected from fluticasone and salmeterol; budesonide and formoterol; ciclesonide and formeterol; beclomethasone and formeterol; fluticasone and formeterol; mometasone and formeterol; ipratropium and salbutamol; fluticasone and vilanterol; mometasone and formeterol; indacaterol and mometasone; arformoterol and ciclesonide; indacaterol and tiotropium; aclidinium and formeterol; darotropium and vilanterol; formoterol and glycopyrrolate; GSK573719 and vilanterol trifenatate; or a pharmaceutically acceptable salt, solvate, hydrate, or polymorph thereof.

In a further aspect, the pharmaceutically active agent is selected from a known class of drug. In a still further aspect, the known class of drug is selected from 5-hydroxytryptamine (5-HT) receptor antagonist, 5-lipoxygenase (5-LO)-activating protein (FLAP) inhibitor, a combination of a β2 adrenergic receptor (ADRB2) agonist and a glucocorticoid receptor (GR) agonist, a combination of a β2 adrenergic receptor (ADRB2) agonist and a leukotriene D4 (LTD4) receptor antagonist, a combination of a β2 adrenergic receptor (ADRB2) agonist and a Mu-Opioid receptor antagonist and a muscarinic M1 receptor antagonist, a combination of a β2 adrenergic receptor (ADRB2) agonist and a muscarinic M3 receptor antagonist, a combination of a β2 adrenergic receptor (ADRB2) agonist and a muscarinic receptor antagonist, a combination of a glucocorticoid receptor (GR) agonist and a histamine H1 receptor antagonist, a combination of a glucocorticoid receptor (GR) agonist and a leukotriene D4 (LTD4) receptor antagonist, a combination of a histamine H1 receptor antagonist and a leukotriene D4 (LTD4) receptor antagonist, a combination of a human leukocyte elastase (HLE) inhibitor and a proteinase 3 (PRTN3) inhibitor, adenosine A1 receptor (ADORA1) antagonist, adenosine A2B receptor (ADORA2B) antagonist, adenosine release inhibitor, adenosine triphosphate (ATP) dephosphorylation, α-adrenergic receptor blocking agents, analgesics, anepileptics, anthelmintics, anti-allergic agents, antiandrogenic agents, antianxiety drugs (anxiolytics), antiarrhythmics, anti-asthma agents, anti-bacterials, antibiotics, antibodies, anti-cancer agents, anti-cholinergics, anticoagulants, anti-convulsants, anti-cytokines, antidepressants, antidiabetic agents, antiemetics, antienteritis agents, antiepileptics, antifungals, antigens, antihistamines, antihypertensives, anti-inflammatories, antimalarials, antimigraine agents, antimuscarinic agents, antimycobacterial agents, anti-narcotic antibodies, antineoplastics, anti-obesity drugs, antioxicants, antiparasitics, antiparkinson agents (dopamine antagononists), anti-spasmodics, antithrombotic agents, antithyroid agents, anti-tussives, antivirals, anxiolytics, appetite suppressants, astringents, β1 adrenergic receptor (ADRB1) antagonist/β2 adrenergic receptor (ADRB2) antagonist, β2 adrenergic receptor (ADRB2) agonist, β-adrenoceptor blocking agents, beta-agonists, biphosphonates, blood products and substitutes, bronchodilators, cardiac inotropic agents, cardiovascular agents, carotenoids, cathepsin S (CTSS) inhibitor, CC Chemokine receptor 3 (CCR3) antagonist, chemokine (C—C motif) receptor 4 (CCR4) antagonist, cell surface antigens and hypoglycaemic agents, central nervous system stimulants, chemoattractant receptor-homologous molecule expressed on TH2 Cells (CRTH2) antagonist, chloride channel Type-2 (ClC-2) Activator, C-Kit receptor tyrosine kinase (CD117) inhibitor, cluster of differentiation 28 (CD28) receptor antagonist, complement inhibitor, contrast media, contrast agents, corticosteroids, cough suppressants (e.g., expectorants and mucolytics), COX-2 inhibitors, cromones, CXC chemokine receptor 2 (CXCR2) antagonist, cytokine receptors, diagnostic imaging agents, diuretics, dopaminergics (anti-parkinsonian agents), elastase 2 neutrophil (ELA2) inhibitor, elastase inhibitors, eoxin inhibitor, E-selectin inhibitor, L-selectin inhibitor, P-selectin inhibitor, glucocorticoid receptor (GR) agonist, glutathione-S-transferase (GST) activator, growth factors, growth supplements, haemostatics, histamine H1 receptor antagonist, histamine H4 receptor antagonist, histamine Release inhibitor, hormonal agents including contraceptives, hormones, human leukocyte elastase (HLE) inhibitor, hypnotics, sedatives, hypoglycemics, immunoglobulin E (IgE) receptor antagonist, immunoglobulins, immunomodulating agents, immunosuppressants, infectious agents, inflammatory mediators, inhibitor of kappa light polypeptide gene enhancer in B-cells/kinase gamma (IKBKG), inhibitor of kappa light polypeptide gene enhancer in B-cells/kinase beta (IKBKB) inhibitor, inhibitor of kappa light polypeptide gene enhancer in B-cells/kinase episolon (IKBKE) inhibitor, integrins, α4 (ITGA4) mRNA inhibitor, interferons, interleukin 13 (IL13) inhibitor, interleukin 4 receptor (IL4R) mRNA inhibitor, interleukin-1 (IL-1) receptor antagonist, interleukin-4 (IL-4) receptor antagonist, interleukin-5 (IL-5) receptor antagonist, interleukin-9 (IL-9) inhibitor, interleukins, kallikrein 1 (KLK1) inhibitor, inhibitor of kappa light polypeptide gene enhancer in B-cells/kinase beta (IKBKB) inhibitor, leukotriene C4 (LTC4) receptor antagonist, leukotriene C4 (LTC4) receptor antagonist/leukotriene D4 (LTD4) receptor antagonist, leukotriene D4 (LTD4) receptor antagonist, leukotriene D4 (LTD4) receptor antagonist/leukotriene E4 (LTE4) receptor antagonist, leukotriene E4 (LTE4) receptor antagonist, leukotriene receptor antagonist, leukotrienes, lipid regulating agents, L-selectin inhibitor, lymphotoxin A (LTA) inhibitor, lymphotoxin A (LTA) inhibitor/tumor necrosis factor-α (TNFα) inhibitor, matrix metalloproteinase (MMP) inhibitor, matrix metalloproteinase-12 (MMP-12) inhibitor, mucolyties, muscarinic M1 receptor antagonist, muscarinic M1 receptor antagonist/muscarinic M3 receptor antagonist, muscarinic M3 receptor antagonist, muscarinic receptor antagonist, muscle contractants, muscle relaxants, myristoylated alanine-rich C-kinase substrate (MARCKS) inhibitor, neoplastics, neuroactive agents, neurokinin NK1 receptor antagonist, neurokinin NK1 receptor antagonist, neurokinin NK2 receptor antagonist, neurokinin NK3 receptor antagonist, neurokinin NK2 receptor antagonist, neurokinin NK3 receptor antagonist, non-opioid analgesic agents, NSAIDs, nuclear factor-κB (NF-κB) inhibitor, nutritional agents and supplements, oncology therapies, p38 alpha mitogen-activated protein (MAP) kinase inhibitor, p38 kinase inhibitor, parasympathomimetics, parathyroid calcitonin, peripheral chemoreceptor agonist, phosphatidylinositol 3-Kinase (PI3K) inhibitor, phosphodiesterase 7 (PDE7) inhibitor/phosphodiesterase-4 (PDE-4) inhibitor, phosphodiesterase-3 (PDE-3) inhibitor, phosphodiesterase-3 (PDE-3) inhibitor/phosphodiesterase-4 (PDE-4) inhibitor, phosphodiesterase-3 (PDE-3) inhibitor/phosphodiesterase-5 (PDE-5) inhibitor, phosphodiesterase-4 (PDE-4) inhibitor, phosphodiesterase-5 (PDE-5) inhibitor, phosphodiesterase-7 (PDE-7) inhibitor, prostaglandin D2 (PGD2) receptor antagonist, prostaglandins, protease serine 8 (PRSS8) inhibitor, protein synthesis inhibitor, proteinase 3 (PRTN3) inhibitor, P-selectin inhibitor, psychic energizers, radio-pharmaceuticals, respiratory drugs, sedatives, semicarbazide-sensitive amine oxidase (SSAO) inhibitor, sex hormones (including steroids), sirtuin 1 (SIRT1) activator, steroids, stimulants and anoretics, superoxide dismutase (SOD) mimetic, sympathomimetic amines, sympathomimetics, thromboxane A2 (TXA2) receptor antagonist, thyroid agents, Toll-like receptor 9 (TLR9) agonist, tranquilizers, transient receptor potential cation channel subfamily A/member 1 (TRPA1) antagonist, tumor necrosis factor-α (TNFα) inhibitor, tumor necrosis factor super family member 4 (TNFSF4) inhibitor, vaccines (including influenza, measles, menigitis, tuberculosis), vasoactive agents, vasodilators, and xanthines; or a pharmaceutically acceptable salt, derivative, solvate, hydrate, or polymorph thereof.

In a further aspect the pharmaceutically active agent is selected from ciprofloxacin, colistin, dihydroergotamine, fluticasone furoate, fluticasone propionate, formoterol, ipratropium, polymyxin B, rifampicin, salbutamol, salmeterol xinafoate, budesonide acetonide, clarithromycin, clinafloxacin, cloxacillin, colistimethate, dihydroergotamine tartrate, dirithromycin, elcatonin, erythromycin, erythropoietin (EPO), factor IX insulin, floxacillin, flurithromycin, insulin, insulin-like growth factor (IGF), insulin tropin, interferon alpha, interferon beta, interferon gamma, levofloxacin, lomefloxacin, low molecular weight heparin (LMWH), methicillin, tobramycin, vancomycin, vasopressin, beclomethasone dipropionate, budesonide, calcitonin, desmopressin, ergotamine, fentanyl citrate, flurisolide, insulin (including substituted insulins and pro-insulins), mometasone furoate, salbutamol sulphate, salmeterol, ipratropium bromide, proinsulin, semi-synthetic insulins, synthetic insulins, x-ray contrast agents, alpha 1 antitrypsin, AZD1419, AZD1981, AZD3199, AZD5069, AZD5423, AZD8683, AZD9164, AZD9668, ciclesonide, cromolyn sodium, darotropium, enokizumab, epinastine hydrochloride, erdosteine, etamiphylline hydrochloride, fenspiride hydrochloride, flunisolide, glycopyrrolate, GSK1325756, GSK159802, GSK2190915, GSK2245840, GSK256066, GSK573719, GSK610677, GSK681323, GSK961081, guaifenesin, GW870086, hydrocortisone sodium succinate, indacaterol, lebrikizumab, levocetirizine dihydrochloride, losmapimod, MABA, mabuterol hydrochloride, masilukast, mecysteine hydrochloride, metaproterenol sulphate, milveterol hydrochloride, montelukast sodium, olodaterol, omalizumab, oxitropium bromide, oxtriphylline, PF184, PF3526299, PF3635659, PF3893787, PF4191834, PF4764793, PF610355, pirbuterol acetate, pranlukast hydrate, procaterol hydrochloride, seratrodast, sodium pyruvate, TD4208, TD5959, theophylline, tofimilast, tulobuterol hydrochloride, vilanterol trifenatate, xylometazoline hydrochloride, zafirlukas, zileuton and analogues, agonists, antagonists, inhibitors; or a pharmaceutically acceptable salt, derivative, solvate, hydrate, or polymorph thereof.

In a further aspect, the pharmaceutically active agent is selected from 13-cis-retinoic acid, 5-fluorouracil, 9-nitrocamptothesin, AB1010, abatacept, acefylline piperazine, acetylcysteine, aclidinium bromide, ACT129968, AEOL10150, AFX300, AGNCA805, AI128, AIR645, alatrofloxacin, albendazole, albendazole sulfoxide, albuterol sulphate, alfaxalone, alfentanil hydrochloride, alkaline phosphatise, almitrine mesylate, alpha 1 antitrypsin, alpha 1 proteinaseinhibitor, alphaprodine hydrochloride, alprostadil, AM103, AM803, ambroxol, AMG157, AMG761, amifloxacin, amikacin, aminofostin, amitriptyline, amoxicillin, AMP4R1RA, ampicillin, amylin, andazithromycin, anileridine, anipamil, anti-CMV antibody, antiepileptics, papavereturn, antithrombin III, AP1500, ARRY006, atenolol, ATL1102, ATL844, AVE0675, AZD1419, AZD1981, AZD3199, AZD5069, AZD5423, AZD8683, AZD9164, AZD9668, azelastine, azidothymidine, azithromycin, azlocillin, AZN6553, aztreonam, bacitracin, baclofen, bambuterol, bambuterol hydrochloride, beclobrate, beclomethasone dipropionate, belomycin, benralizumab, benzocaine, benzodiazepines, β-carotene, β endorphin, β interferon, bezafibrate, bezitramide, BI671800, bimosiamose disodium, binovum, BIO11006, biperiden, bispecific antibody, bisphosphonates, BMS639623, bromazepam, bromocriptine, bucindolol, budesonide, budesonide acetonide, buflomedil, bupivacaine, buprenorphine hydrochloride, busulfan, butorphanol tartrate, cadralazine, caffeine, calcitonin, camptothesin, canakinumab, canceractivity, canthaxanthin, capreomycin, captopril, carbamazepine, carbenicillin, carbocysteine, carboprost, carfentanil citrate, carmoterol, CAT354, cefaclor, cefadroxil, cefalexin, cefalotin, cefamandole, cefatrizine, cefazedone, cefazolin, cefepime, cefinenoxime, cefixime, cefluoroxime, cefinetazole, cefonicid, cefoperazone, ceforanide, cefotaxime, cefotetan, cefoxitin, cefpodoxime, cefprozil, cefsulodin, ceftazidime, ceftbuten, ceftizoxime, ceftriaxone, cefuroxime, CEM315, cephacetrile, cephalexin, cephaloglycin, cephaloridine, cephalothin, cephapirin, cephradine, ceredase, cerezyme, CHF5480, chlorambucil, chromoglycinic acid, ciclesonide, ciclonicate, ciglitazone, cillin, cintredekin besudotox, ciprofloxacin, ciramadol, clarithromycin, clenbuterol, clenbuterol hydrochloride, clinafloxacin, clonidine, clopiogrel, cloxacillin, cobiprostone, codeine, colistimethate, colistin, cortexolone, corticosterone, cortisol, cortisone, CP325366, CP4166, c-peptide, cromolyn sodium, CS003, CWF0710, cyclophosphamide, cyclosporine A and other cyclosporins, cytarabine, dantrolene, daptomycin, darotropium, davercin, deoxyribonuclease (Dnase), desmopressin, desocryptin, desogestrel, dexamethasone, dextromoramide, dextropropoxyphene, dezocine, diamorphine hydrochloride, diazepam, diclofenac, dicloxacillin, dideoxyadenosine, dideoxyinosine, digitoxin, digoxin, dihydrocodeine, dihydroergotamine, dihydroergotamine tartrate, dihydroergotoxin, diltiazem, DIMS0001, dipipanone hydrochloride, dirithromycin, disodium pamidronate, dopamine antagonists, doxofylline, doxorubicin, DRL2546, DW403, DX2300, econazole, EL246, Elafin, ELB353, elcatonin, enadoline, enalapril, endothelial growth factors, endralazine, enkephalin, enokizumab, enoxacin, EP101, EPI12323, epinastine hydrochloride, epoprostenol, eptazocine hydrobromide, erdosteine, ergotamine, erythromycin, erythropoietin (EPO), estradiol, estramustine, etamiphylline hydrochloride, ethoheptazinecitrate, ethylmorphine hydrochloride, etofibrate, etoposide, etorphine hydrochloride, ETX9101, factorix, factor IX insulin, factor viii, felbamate, fenbendazole, fenofibrate, fenoterol, fenspiride hydrochloride, fentanyl citrate, fexofenedine, FHTCT4, flecamide, fleroxacin, floxacillin, flunarizin, flunisolide, flurazepam, flurbiprofen, flunisolide, flurithromycin, Fluticasone furoate, fluticasone propionate, follicle stimulating hormone (FSH), formoterol, fosfomycin, fosmidomycin, furosemide, galampicillin, gallopamil, gamma interferon, gatifloxacin, gentamicin, gepefrine, ghrelin, glial growth factor (GGF), gliclazide, glipizide, glucagon-like peptide 1 (GLP-1), glucagon-like peptide thymosin alpha1, glycopyrrolate, gramicidin, granulocyte colony stimulating factor (GCSF), granulocyte macrophage colony stimulating factor (GMCSF), GRC3886, grepafloxacin, griseofulvin, growth colony stimulating factor, growth hormone, growth hormone releasing hormone (GHRH), GSK1325756, GSK159802, GSK2190915, GSK2245840, GSK256066, GSK573719, GSK610677, GSK681323, GSK961081, guaifenesin, GW870086, HAE1, haptoglobulin, HC030031, heparin, hepatitis B vaccine, hetacillin, HF1020, HI164OV, HL028, HMT, HS-A1, human growth hormone (HGH), hydralazine, hydrochlorothiazide, hydrocodone, hydrocortisone, hydrocortisone sodium succinate, hydromorphone hydrochloride, hydroxyzine, hyoscine, ibuprofen, ibuproxam, IC485, IL-4 inhibitor COSMIX, IMA026, IMD1041, imipenem, IMO2134, indacaterol, indinavir, indomethacin, INDUS82010, insulin, insulin (including substituted insulins and pro-insulins), insulin-like growth factor (IGF), insulin tropin, interferon alpha, interferon beta, interferon gamma, interleukin-1, interleukin-1 receptor, interleukin-1 receptorantagonist, interleukin-2, interleukin-3, interleukin-4, interleukin-4R, interleukin-6, iodamide, ipratropium, ipratropium bromide, irloxacin, josamycin, kanamycin, keratinocyte growth factor (KGF), ketamine, ketobemidone, ketoconazole, ketoprofen, ketotifen, ketotifen fumarate, KM278, KPE06001, K-strophanthin, L971, labetalol, lactobacillus vaccine, LAS 100977, lebrikizumab, leucomycin, leuprolide, leutinizing hormone releasing hormone, levocetirizine dihydrochloride, levofloxacin, levomethadone hydrochloride, levomethadyl acetate, levorphanol tartrate, lidocaine, lidoflazin, lignocaine, lisuride, lisuride hydrogen maleate, LMP 160, lomefloxacin, loracarbef, lorazepam, losmapimod, lovastatin, low molecular weight heparin (LMWH), luteinizing hormone releasing hormone (LHRH), MABA, mabuterol hydrochloride, macrophage colony stimulating factor (M-CSF), masilukast, MDT011, mecysteine hydrochloride, MEDI557, mefenamic acid, melphalan, MEM1414, memantin, meptazinol hydrochloride, meropenem, mesulergin, metaproterenol sulphate, metergoline, methadone hydrochloride, methicillin, methotrexate, methotrimeprazine, methyldigoxin, methylprednisolone, metipranolol, metisoprenol, metkephamide, metolazone, metoprolol, metoprolol tartrate, metronidazole, mexiletine, mezlocillin, mianserin, miconazole, miconazole nitrate, midazolam, midecamycin, mideplanin, milveterol hydrochloride, minoxidil, miocamycin, misonidazol, MK6105, MLN6095, MMP protease inhibitor, molsidomin, montelukast, montelukast sodium, morphine, moxalactam, moxifloxicin, nadolol, nafazatrom, nafcillin, nafiverine, nalbuphine hydrochloride, naproxen, natural insulins, NCX1020, nedocromil, neomycin, nerve growth factor (NGF), nesapidil, netilmicin, nicardipine, nicomorphine hydrochloride, nicorandil, nifedipine, niludipin, nimodipine, nitrazepam, nitrendipine, nitrocamptothesin, norfloxacin, NPB3, OC000459, octreotide, ofloxacin, olanzapine, oleandomycin, olodaterol, omalizumab, opium, OPLCCL11LPM, OX2477, OX40, OX914, oxacillin, oxazepam, oxitropium bromide, oxprenolol, oxtriphylline, oxycodone, oxymorphone hydrochloride, oxytetracycline, oxytropium bromide, thiazinamide chloride, PA401, paracetamol, paramecin, parathyroid hormone (PTH), parogrelil hydrochloride, pazufloxacin, pefloxacin, penecillin O, penicillin G benethamine, penicillin G, penicillin V, Pentamidine, pentamidine isethiouate, pentamorphone, pentazocine, PEP03, pethidine hydrochloride, PF184, PF3526299, PF3635659, PF3893787, PF4191834, PF4764793, PF610355, phenazocine hydrobromide, phenopendine hydrochloride, phenothiazines, phenylbutazone, phosphodiesterase (PDE) compounds, picenadol hydrochloride, picotamide, pindolol, piperacillin, piposulfan, pirbuterol, pirbuterol acetate, piretanide, piribedil, piritramide, piroxicam, pirprofen, PLA950, plasminogenici activator, POL6014, polymyxin B, pranlukast hydrate, prednisolone, prednisone, pregnenolone, procarbacin, procaterol, procaterol hydrochloride, progesterone, proinsulin, propafenone, propanolol, propentofyllin, propiram fumarate, propofol, propranolol, prulifloxacin, PS291822, PT002, PT003, PT009, PT010, PUP1, PXS4159, PXS74, QAX028, QAX576, R7103, raloxifene, rampolanin, RBx11082, REGN668, remifentanil hydrochloride, reproterol, respiratory syncytial virus antibody, RG7449, rifampicin, rifapentin, rokitamycin, roxithromycin, RPL554, RTA403, salbutamol sulphate, salbutamol, salmeterol, salmeterol xinafoate, SAR21609, SAR389644, SB656933, SCH527123, semi-synthetic insulins, seratrodast, simvastatin, sitafloxacin, sobrerol, sodium pyruvate, sodium, cromoglycate, somastotine, somatostatin, somatropin, sparfloxacin, spiradoline mesylate, spiromycin, stilamine, STNM03, streptomycin, sufentanil citrate, sulfinalol hydrochloride, sulfinpyrazone, suloctidil, sulproston, suprofen, swinolide A, synthetic insulins, TA106, talinolol, TAPI, TARGALLERG I200, TARGALLERG I201, TARGALLERG I202, taxol, taxotere, tazanolast, TD4208, TD5959, teicoplanin, temafloxacin, terbutaline, testosterone, testosterone propionate, testosterone undecanoate, tetomilast, tetracane HI, theophylline, thrombopoietin (TPO), tiaramide hydrochloride, ticarcillin, tilidate hydrochloride, tissue growth factors, tobramycin, tofimilast, tolmetin, tonazocine mesylate, tosufloxacin, TPI1100, TPI2200, tramadol hydrochloride, tranilast, trefentanil, triamcinolone acetamide, triquilar, troleandomycin, tromantadine hydrochloride, trovafloxacin, TT32, tulobuterol hydrochloride, tumor necrosis factor (TNF), UR5908, UR63325, urokinase, VAK694, valium, vancomycin, vasopressin, verapamil, vidarabine, vidarabine phosphate sodium salt, vilanterol trifenatate, vinblastine, vinburin, vincamine, vincristine, vindesine, vinpocetine, vitamin A, vitamin E succinate, VLA-4 inhibitors, X072NAB, X-ray contrast agents, xylometazoline hydrochloride, zafirlukast, and zileuton including analogues, agonists, antagonists, inhibitors; or a pharmaceutically acceptable salt, derivative, solvate, hydrate, or polymorph thereof.

In reference to peptides and proteins, a therapeutic peptide or protein is inclusive of synthetic, native, glycosylated, unglycosylated, pegylated forms, and pharmaceutically active agent fragments and analogs thereof.

A description of the above classes of pharmaceutically active agents and a listing of individual therapeutic agents within each class can be found in Martindale's *The Extra Pharmacopoeia,* 31st Edition (The Pharmaceutical Press, London, 1996), specifically incorporated by reference. Alternative, a description and listing of suitable pharmaceutically active agents can be found in *Physicians Desk Reference* (60th Ed., pub. 2005). The disclosed pharmaceutically active agents are either commercially available and/or can be prepared by techniques known in the art. An exhaustive list of drugs for which the methods of the invention are suitable would be burdensomely long for this specification; however, reference to the general pharmacopoeia listed above would allow one of skill in the art to select appropriate pharmaceutically active agents which can be used to prepare the disclosed composite particles comprising a millable grinding matrix and a pharmaceutically active agent. It is also expected that new pharmaceutically active agents, including novel chemical entities (NCE) and other therapeutic agents for which the disclosed methods are suitable will be created or become commercially available in the future.

What is claimed is:

1. A method for making inhalable composite particles comprising a pharmaceutically-active agent, the method comprising:

a) dry milling a composition comprising a solid pharmaceutically active agent and a millable grinding matrix in a mill comprising a plurality of milling bodies for a time period sufficient to produce composite particles comprising the millable grinding matrix and the solid pharmaceutically-active agent, wherein the pharmaceutically-active agent has median particle size on a volume basis between 50 nm and 1,000 nm subsequent to milling, as measured by laser diffraction; and b) milling the composite particles in a mill without milling bodies for a time period sufficient to produce inhalable composite particles having a volume weighted mean diameter (D4,3) between 1,000 nm and 10,000 nm, as measured by laser diffraction, and wherein the step of milling in mill without milling bodies reduces the size of the composite particles without reducing the median particle size of the pharmaceutically active agent.

2. The method of claim 1, wherein 90% of the inhalable composite particles, determined on a particle volume basis, have a diameter less than or equal to 15,000 nm.

3. The method of claim 1, wherein 90% of the inhalable composite particles, determined on a particle volume basis, have a diameter greater than or equal to 2000 nm.

4. The method of claim 1, wherein the mill without milling bodies is selected from a jet mill and air jet mill.

5. The method of claim 1, wherein the millable grinding matrix comprises a carbohydrate or an amino acid.

6. The method of claim 5, wherein the carbohydrate is selected from the group consisting of: mannitol, sorbitol, xylitol, maltitol, lactitol, erythritol, arabitol, ribitol, glucose, fructose, mannose, galactose, lactose, sucrose, raffinose, ribitol, maltose, sorbose, cellobiose, sorbose, trehalose, a maltodextrin, a dextran, inulin, and 1-O-alpha-D -glucopyranosyl-D-mannitol.

7. The method of claim 5, wherein the amino acid is selected from the group consisting of: aspartic acid, glutamic acid, leucine, L-leucine, isoleucine, lysine, valine, methionine, phenylalanine, glycine, arginine, aspartic acid, glutamic acid, cysteine, alanine, serine, phenylalanine, lysine, and N-acetyl-L-cysteine.

8. The method of claim 6, wherein the millable grinding matrix comprises lactose and at least one compound selected from the group consisting of: sodium chloride, anhydrous lactose, mannitol, glucose, sucrose, trehalose, sorbitol, 1-O-alpha-D-glucopyranosyl-D-mannitol, xylitol, maltitol, lactitol, erythritol, arabitol, ribitol, fructose, mannose, galactose, raffinose, ribitol, maltose, sorbose, cellobiose, sorbose, inulin, sodium citrate, sodium ascorbate, lecithin, soy lecithin, dipalmitoyl phosphatidylcholine, phosphatidylglycerol, dipalmitoyl phosphatidyl ethanolamine, dipalmitoyl phosphatidylinositol, phospatidylcholines, hosphatidylethanolamine, phosphatidylglycerols, phosphatidylinositol, phosphatidylserine, sodium lauryl sulphate, magnesium lauryl sulphate; leucine, L-leucine, isoleucine, lysine, valine, methionine, phenylalanine, glycine, arginine, aspartic acid, glutamic acid, cysteine, alanine, and serine.

* * * * *